(12) United States Patent
Haberman et al.

(10) Patent No.: US 10,984,912 B2
(45) Date of Patent: Apr. 20, 2021

(54) METHOD AND APPARATUS TO MONITOR, ANALYZE AND OPTIMIZE PHYSIOLOGICAL STATE OF NUTRITION

(76) Inventors: Seth Haberman, New York, NY (US); Joseph Bernstein, Haverford, PA (US)

( * ) Notice: Subject to any disclaimer, the term of this patent is extended or adjusted under 35 U.S.C. 154(b) by 0 days.

(21) Appl. No.: 13/042,694

(22) Filed: Mar. 8, 2011

(65) Prior Publication Data

US 2011/0218407 A1 Sep. 8, 2011

Related U.S. Application Data

(60) Provisional application No. 61/311,614, filed on Mar. 8, 2010.

(51) Int. Cl.
*G16H 50/20* (2018.01)
*G16H 20/60* (2018.01)
*G16H 40/67* (2018.01)

(52) U.S. Cl.
CPC ............. *G16H 50/20* (2018.01); *G16H 20/60* (2018.01); *G16H 40/67* (2018.01)

(58) Field of Classification Search
CPC ..... G06C 50/22; G06C 50/24; G06F 19/3475; G06F 19/3481; G06F 19/00; G06F 19/3456; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00; G16H 50/20; G16H 50/70; G16H 50/50; A63B 24/0075; G09B 19/0092

(Continued)

(56) References Cited

U.S. PATENT DOCUMENTS 8,398,546 B2 3/2013 Pacione et al.
2003/0208113 A1* 11/2003 Mault .................... G16H 40/63
600/316

(Continued)

FOREIGN PATENT DOCUMENTS

EP 2040211 A1 3/2009
WO WO 2008001366 A2 * 1/2008

OTHER PUBLICATIONS

European Patent Application No. 11753906.4, EP Communication (Office Action), dated Sep. 23, 2015, 11 pages.

*Primary Examiner* — Joseph D Burgess
(74) *Attorney, Agent, or Firm* — Seyfarth Shaw LLP; George Haight

(57) ABSTRACT

A method and apparatus that for monitoring the physiological state of nutrition of an individual and adaptively analyze that data input to anticipate the individual's nutritional needs. A satiety meter may be employed to analyze a user's profile including nutritional state and determine when and how much a user should consume to prevent the onset of hunger and communicate is to a decision engine. The decision engine may generate and communicate a message to the user via the client device to prescribe prophylactic intake of nutrition to the individual prior to the onset of hunger based on the user's nutrition plan and/or regimen.

7 Claims, 13 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 2005/0113649 A1* | 5/2005 | Bergantino | ......... G06F 19/3475 |
| | | | 600/300 |
| 2006/0014124 A1* | 1/2006 | Manu | ........................... 434/236 |
| 2006/0064037 A1* | 3/2006 | Shalon | ................... G16H 20/60 |
| | | | 600/586 |
| 2006/0074279 A1 | 4/2006 | Brower | |
| 2006/0074716 A1* | 4/2006 | Tilles et al. | ....................... 705/2 |
| 2007/0179349 A1* | 8/2007 | Hoyme et al. | ................ 600/300 |
| 2008/0162352 A1* | 7/2008 | Gizewski | ............ G06F 19/3456 |
| | | | 705/50 |
| 2009/0075781 A1 | 3/2009 | Schwarzberg et al. | |

* cited by examiner

METHOD AND APPARATUS TO MONITOR, ANALYZE AND OPTIMIZE PHYSIOLOGICAL STATE OF NUTRITION

CROSS REFERENCES TO RELATED APPLICATIONS

This application claims the benefit of U.S. Provisional Patent Application Ser. No. 61/311,614, filed on Mar. 8, 2010, the contents of which are incorporated herein by reference in their entirety.

FIELD

The disclosure generally relates to diet, appetite and nutrition. More specifically, the disclosure relates to the monitoring and analysis of an individual's physiological and mental state of nutrition and appetite, and providing user feedback to achieve desired goals.

BACKGROUND

In the United States, approximately 66% of the adult population (≥20 years) has been classified as either overweight or obese, and many health problems and chronic diseases can be partially or completely attributed to these two factors. Ogden, C. L., Carroll, M. D., Curtin, L. R., McDowell, M. A., Tabak, C. J., Flegal, K. M. *Prevalence of overweight and obesity in the United States,* 1999-2004. JAMA. 2006 Apr. 5; 295(13):1549-55. For example, obesity is implicated in many types of cardiovascular disease (CVD), which represents the leading cause of mortality (871,517 deaths in 2004) in the United States. Rosamond et al., American Heart Association Statistics Committee and Stroke Statistics Subcommittee; *Heart disease and stroke statistics*—2007 *update: a report from the American Heart Association Statistics Committee and Stroke Statistics Subcommittee.* Circulation. 2007 Feb. 6; 115(5):e69-171. Additionally, research indicates that obesity is implicated in as many as one third of all cancers, which represent the second leading cause of mortality in the United States (American Cancer Society). Wolk, A., Gridley, G., Svensson, M., Nyren, O., McLaughlin, J. K., Fraumeni, J. F., Adam, H. O. A prospective study of obesity and cancer risk (Sweden). *Cancer Causes Control.* 2001 January; 12(1):13-21. Furthermore, obesity is implicated in many chronic diseases such as hypertension and Type 2 diabetes. Burton, B. T., Foster, W. R., Hirsch, J., Van Itallie, T. B. *Health implications of obesity: an NIH Consensus Development Conference.* Int J Obes. 1985; 9(3):155-70. Obesity related diseases have a significant monetary impact on the world health system: CVD alone was estimated to cost the United States health care system $431.8 billion in 2004. Rosamond et al., 2007.

Since the majority of these disease states are causally linked to obesity, they may be either mitigated or prevented by simply altering the diet, nutrition and appetite of an affected individual. The concept of weight loss by diet regimen is well known in the art. Prior art systems of weight management can be broadly divided into several types.

One type essentially tells an individual what to eat. For example, U.S. Pat. No. 5,683,251 provides a method for teaching children about various food groups so that they may learn about proper nutrition. An approach designed for adults is presented in U.S. Pat. No. 6,336,136, which provides a computer program that determines a weight reduction program (i.e. choosing appropriate meals) for an individual based on a variety of data that can be input by the user.

Another type consists of systems of prepackaged food that give an individual specific food to eat, for example, as mentioned in U.S. Pat. Nos. 6,102,706, 5,994,295, and U.S. Publication No. 20050118233.

Another type assists an individual in maintaining a previously established diet plan. For example, U.S. Publication No. 20070208593 provides a computer based system that accepts user input about current eating habits and provides feedback and encouragement about the user's progress towards defined weight loss goals. Similarly, U.S. Publication No. 20060058586 provides a computer based program that monitors an individual's diet over time, and then suggests alternative dietary consumption that is in line with the individual's goals. U.S. Publication No.: 20070135266 provides a computer based system that accepts user input about current eating habits and/or exercise level and provides feedback and encouragement to the user about what foods to eat and not to eat. Further, CA Patent No. 514,822 teaches a devices that monitors caloric intake based on a chart of food group listings and helps the user to follow an established diet plan.

U.S. Publication No. 20050096637 (hereafter the '637 publication) references several different medical device/sensors that measure physiological parameters that vary with food intake (e.g. core body temperature, glucose, trans-abdominal impedance, electrical activity of the gastrointestinal tract, and physical motion). The '637 publication discloses a system comprising:

"a sensor to sense a physiological parameter of a patient that changes as a function of a quantity of food consumed by a patient; a processor to estimate the quantity of food consumed by the patient as a function of the sensed physiological parameter and to generate a control signal to control a drug delivery system as a function of the estimation; and the drug delivery system configured to deliver a drug to a body of the patient in response to the control signal."

The '637 publication describes a reactive system that responds to a change in food consumption by delivering an appropriate drug. The sensors of the '637 publication are not configured in a system that addresses nutritional states relevant to diet/weight-loss regimens. Furthermore, the system of the '637 publication does not in any way address other nutrition or appetite related goals.

U.S. Pat. No. 5,673,691 (hereafter the '691 patent) discloses a hand-held micro-computer weight control device that is used by a single user. The device in the '691 patent accepts user input of physical characteristics and goals to be reached. The device in the '691 patent monitors the user's physical characteristics, exercise, and caloric intake and provides feedback regarding the user's progress and may adjust the user's program in response to the user's adherence to the goals, such as by lowering or raising the caloric intake recommended to the user. The '691 patent also incorporates behavior modification procedures such as stimulus control, prompting, shaping, goal setting, and feedback into a weight loss program designed to change the nutrition and exercise habits of the user. The device generates visual and audio prompts to signify times to eat, drink water and exercise, prescribes what to eat and in what quantities, and duration of exercise. The affect of the '691 patent's program is that by following the prompts of the device, the user develops a structured routine of eating meals at consistent times, exercising three times per week, weighing daily, and drinking water at regular intervals throughout the day.

The '691 patent discloses a single user device that prompts a user to eat, drink water and exercise at specific times to enable the user to develop a structured and consistent routine. The '691 patent does not disclose monitoring the physiological state of nutrition of an individual and adaptively analyzing that data to anticipate the individual's nutritional needs and prompt the individual to eat and/or drink prior to the onset of hunger. The '691 patent does not use physiological or behavioral and attitudinal data, rather it uses physical data such as age, height, and weight to monitor the user. The '691 patent involves a single user device and therefore does not use third party data that may be adapted and incorporated into the user's experience.

Generally, the prior art systems and/or methods are based on general rules (i.e. total calorie intake or % carbohydrate intake) and fail to account for variations in individual physiology, nor do they consider concurrent physiological requirements, behavioral and/or attitudinal factors relating to the individual. They do not monitor what the individual is eating on a real-time basis. They only provide limited instructive feedback to the individual based on generally static information and parameters. They do not consider successes or modify rules based on successes of rules over time based on information from the individual or like individuals. Furthermore and very significantly, they do not preemptively prescribe nutritional measures or instruction that is tailored to an individual's physiology and demands as a prophylactic to overeating and in turn poor health/nutritional behavior.

SUMMARY

Embodiments of the disclosure provide a method and apparatus for monitoring the physiological state of nutrition and the attitudinal state of an individual and adaptively analyzing data input to anticipate the individual's nutritional and psychological needs. A central problem with existing diet/weight-loss art is that people start to eat for reasons of hunger, but they do not necessarily stop once their nutritional needs are met. The control of hunger involves a complex feedback loop between the upper digestive tract (stomach and small intestine) and the various regions of the brain, for example the hypothalamus region of the brain. There is an inherent time lag in this system, thus it is possible for an individual to eat more than is necessary before the signaling molecules of the upper digestive tract are able to relay the sense of "fullness" to the brain and allow the brain to modulate behavior accordingly, i.e. stop eating. Similarly, the nutritional state of an individual can become too low before a "normal" sense of hunger is initiated, opening the possibility of a large nutritional deficit ("I'm starving!") and over-compensation for that deficit (for example, resulting in gluttonous eating). Lastly, a deficit in only one form of nutrition (for example, simple carbohydrates) may provoke over-eating across many categories. Embodiments of the present disclosure seek to solve these problems by monitoring an individual's state of nutrition and appetite at the physiological level, anticipating deficits, and prescribing prophylactic intake of nutrition to the individual prior to the onset of hunger. In this regard, embodiments of the present disclosure are proactive, rather than reactive. The present disclosure responds to a change in nutritional physiology or a calculated regression of what is estimated to be the physiology preempting exaggerated and problematic responses.

Illustrative embodiments of the present disclosure provide a monitoring method and apparatus for accepting and analyzing physiological input from a user for a variety of indicia of hunger and related psychological states. The illustrative embodiments of the present disclosure establish a physiological, behavioral and attitudinal baseline for the individual. Once created, the baseline may be used to establish an adaptive feedback loop that can be used to monitor and regulate the user's nutritional intake by comparing the user's current physiological indicia of hunger and attitude to the user's established baseline(s), and prescribing an appropriate course of action. The adaptive nature of the feedback loop allows the monitoring method and apparatus to be tailored to the unique nutritional physiology, and behavioral and attitudinal needs of the user for positive and negative reinforcement.

Physiological inputs that may be monitored include, but are not limited to, blood sugar level, temperature, electrolyte level, and/or oxygen level. Additionally, the physiological inputs may also include any of a variety of endogenous upper digestive feedback signals that normally regulate eating such as ghrelin, cholecystokinin, leptin, insulin, glucagon, and/or amylin. Attitudinal and behavioral inputs may include self descriptions of hunger, attitudes towards nutrition and weigh lost and the degrees of positive and negative feelings towards the guidance program, and speed of response to queries and specific tactile measures on touch screens.

Illustrative embodiments of the method and apparatus to monitor and analyze the physiological state of nutrition and appetite, and the behavioral and attitudinal states of an individual and optimize nutritional intake include a computer based system. The computer based system includes one or more server computers, a network interconnecting the server computer(s) or data processing device(s) with one or more databases, and one or more electronic communication or client devices that can access, provide, transmit, receive, and modify information over a wired or wireless network. The computer based system is in communication with the client device of one or more user's/client's. The client device(s) may be continually connected to the computer based system or separate/disconnected from the computer based system. The client device(s) may be an electronic communication device such as but not limited to a personal computer, personal digital assistant (PDA), cellular or mobile phone, and other devices that can access, provide, transmit, receive, and modify information over wired or wireless networks. The network may be a local area network or a wide area network and may be a private or public network of any size or scope. In an illustrative embodiment, the network is the Internet.

In an illustrative embodiment, the computer based system receives input data from a client and/or user via the client device. The input data from the user may be stored in a profile database within or linked to the computer based system. The input may include information about the user's physical characteristics, personal calendar plans or links to information about calendar plans and other links to allow the continuous update of information about the user's affairs, physiological characteristics, current food consumption, carbohydrate intake, caloric intake, exercise activity, attitude, behavior, hunger levels, immediate past and present goals, progress, and type of nutrition plan the user may desire to follow. Further, the input may include running data, which the user may input and/or update periodically throughout the day, such as but not limited to the user's physiological characteristics, psychological characteristics, current food consumption, carbohydrate intake, caloric intake, exercise activity, attitude, behavior, and hunger levels. This data may also be received from various monitoring devices directly collection input from the user's body.

The computer based system may include a nutrition regimen template database and/or processor. The nutrition regimen template database may include nutrition regimen templates that include well known diet regimens and may be extensible, customizable, and parameterizable to accommodate learning and adjustment based on the user's input data. The nutrition regimen templates may be extensible and customizable based on the user's profile including but not limited to the user's input data, civil holidays, religious beliefs, personal calendar, and personal goals as well as the efficacy of the nutrition regimen in progress.

The computer based system may include a decision engine and/or a progress tracker. The decision engine may analyze and monitor the user's input data and provide feedback, recommendations, suggestions and messages to the user via the client device. The progress tracker may be integrated with or in communication with the decision engine. The progress tracker may receive user input data from the decision engine and track the weight and nutritional status of the user over time. It is well known in the art that the nutritional status of an individual is not given solely by the user's parameters at an instant but rather over the course of these parameter's variation over time, for example, a 90 kg person who has never lost weight is physiologically different than a 90 kg person who is down from 110 kg over the last 3 months. The latter represents a monthly loss of approximately 6% of body mass, and will provoke an "anti-starving" physiological response. Thus, the progress tracker, to measure where the user is going needs a representation of where the user came from.

Most sophisticated eating regimens include multiple phases with a minimum usually being an intense period of establishing rules and then a maintenance period. For instance, in the Atkins Diet there are four phases which are induction, ongoing, pre-maintenance and maintenance. Usually the greatest progress is made during the initial period and then foods are gradually added back into the diet regimen when some of the goals are realized. Transition from one phase to another is usually only based on weight goals and is often lost in the next cycle as the user and the diet haven't properly adapted. And even a four phase approach is only a crude approximation of the changes in the user's biology and metabolism; hence in the system and method according to the invention progress is "tracked" continuously and instantaneously and includes a large number of other factors beyond weight.

The progress tracker not only measures the individual's progress against the user's initial goals and moves the individual through phases of the nutrition regimen, but monitors the user's progress against other goals, for example emotional connection to food, behavior at parties and events. Additionally, as experience is gained the nutrition regimen evolves to best suit the individual during the particular circumstance of the user's life and the world around the user. The progress tracker is also a user output cue to indicate the user's success not just in accomplishing weight-loss but in adhering to the outlined nutrition regimen. The progress tracker also provides feedback to the user, such as, but not limited to accolades acknowledging success with regard to avoiding a certain food or drink at an event, or accolades on progressing a day without failing. These incremental positive messages focus on behavior as well as accomplishments in the context of an adapted nutrition and behavior regimen.

The computer based system may store third party data which in aggregate is designated "crowd data", which is data collected by the system based on others who have used the system, in a database within or linked to the computer based system. The third party data may be analyzed to determine what has worked for others, in the past. The third party data, especially data of profiles related to the user may be incorporated into the user's experience to provide the most effective experience for the particular user. The combination of the user's input and third party data may create an aggregated profile, which may be stored in a database within or linked to the computer based system.

The computer based system may include one or more modules, programs, or processors, such as but not limited to a binge preventer, a satiety meter, a learning process and motivation system. The binge preventer may be in communication with the decision engine. The binge preventer may receive the user's input data from the decision engine, such as but not limited to information about the user's personal calendar events, physiological characteristics, attitude, behavior and like data for like profiles. The binge preventer may analyze and monitor such data and attempt to determine when a user may experience a situation where the user may be tempted to binge. Further, the binge preventer may establish the correct psychological framework and determine when a user has engaged in a binge and adjust the user's nutrition regimen to correct or mitigate such binge. The binge preventer will also, if a binge occurs focus the proper motivational messages to terminate the binge.

The satiety meter may be in communication with the decision engine. The satiety meter may receive the user's input data from the decision engine, such as but not limited to the user's physiological characteristics, current food consumption, carbohydrate intake, caloric intake, exercise activity, attitude, and behavior. The satiety meter may be linked to a rules database, which may contain scientific data and algorithms for enduring and healthful weight loss that may be applied to the user's input data to determine the user's nutritional needs and what and when the user should consume to prevent the user from experiencing the onset of hunger.

The learning process may receive the user's input data and progress data, third party data, and/or the aggregated profile. The learning process may analyze and monitor the data. The learning process may modify and/or update the parameters of the nutrition and appetite plan based on the progress and/or adaptation of the user to the plan as well as other aspects of the system. For example, the learning process may modify the parameters of the satiety meter and/or the parameters of the decision engine to optimize the user's weight loss plan, and/or update the user's profile or progress data based on the observed success or failure of the user or like users thus far.

The motivation system maintains a model that generates motivational messages based on the users inputs from a library of messages. The system will refine the types, tempo and means of representation of those messages in concert with the learning system to achieve maximum effectiveness. It is understood that this may change during the different phases of a nutrition or regiment and that the system must be continually adaptive.

The motivation system may include a message calculator that interacts with a message database. The message database may include template messages, and/or new messages created based on user and third party data. The motivation message calculator may analyze the user's profile including the user's nutrition and appetite state and calculate and/or determine a motivational message to be sent to the user, via the client device, to encourage the user to stay on track and/or prevent the user from engaging in a certain course of action. The message calculator may incorporate the science of psychology and/or results of third party data to formulate a motivational message to be sent to the user via the client device. The motivation message calculator selects the message, the message delivery type (including but not limited to graphical, spoken, written), the timing and frequency to maximize impact. The decision engine may accept data and/or information from any of the above processors and databases such as but not limited to the user's input, the progress tracker, the binge preventer, the satiety meter, the learning process, the message calculator, and nutrition regimen template database and/or processor. The decision engine may compile the information received and determine the next course of action the user should take, such as what to consume, when to consume, and/or transmit recommendations, suggestions, and motivational messages to the user via the client device.

In other illustrative embodiments, the disclosure may be embodied in the form of computer program code containing instructions embodied in tangible media, such as floppy diskettes, CD-ROMs, hard drives, or any other computer-readable storage medium, wherein, when the computer program code is loaded into and executed by a computer. The monitoring method and apparatus may be used to facilitate the weight loss and/or maintenance regimen of a particular user. In another embodiment, the monitoring method and apparatus may be implemented in one or more Application Specific Integrated Circuits (ASICs) and/or may be used to facilitate specific nutrition and appetite goals of a user. The monitoring method and apparatus may be used to streamline nutrition intake for specific goals like bodybuilding (development of muscle mass), athletic conditioning (development of muscle strength or endurance), reducing the risk of heart attack, or controlling nutrition and appetite for persons with dietary restrictions, such as diabetes.

Although the computer based system is described herein as having more than one database and processor, it should be appreciated that the computer based system may include a single processor and database that may perform all the functionality as described herein.

BRIEF DESCRIPTION OF THE DRAWINGS

The present disclosure is illustrated in the figures of the accompanying drawings which are meant to be exemplary and not limiting, in which like references are intended to refer to like or corresponding parts, and in which.

DETAILED DESCRIPTION

Detailed embodiments of the present disclosure are set forth herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present disclosure.

Figure 1:
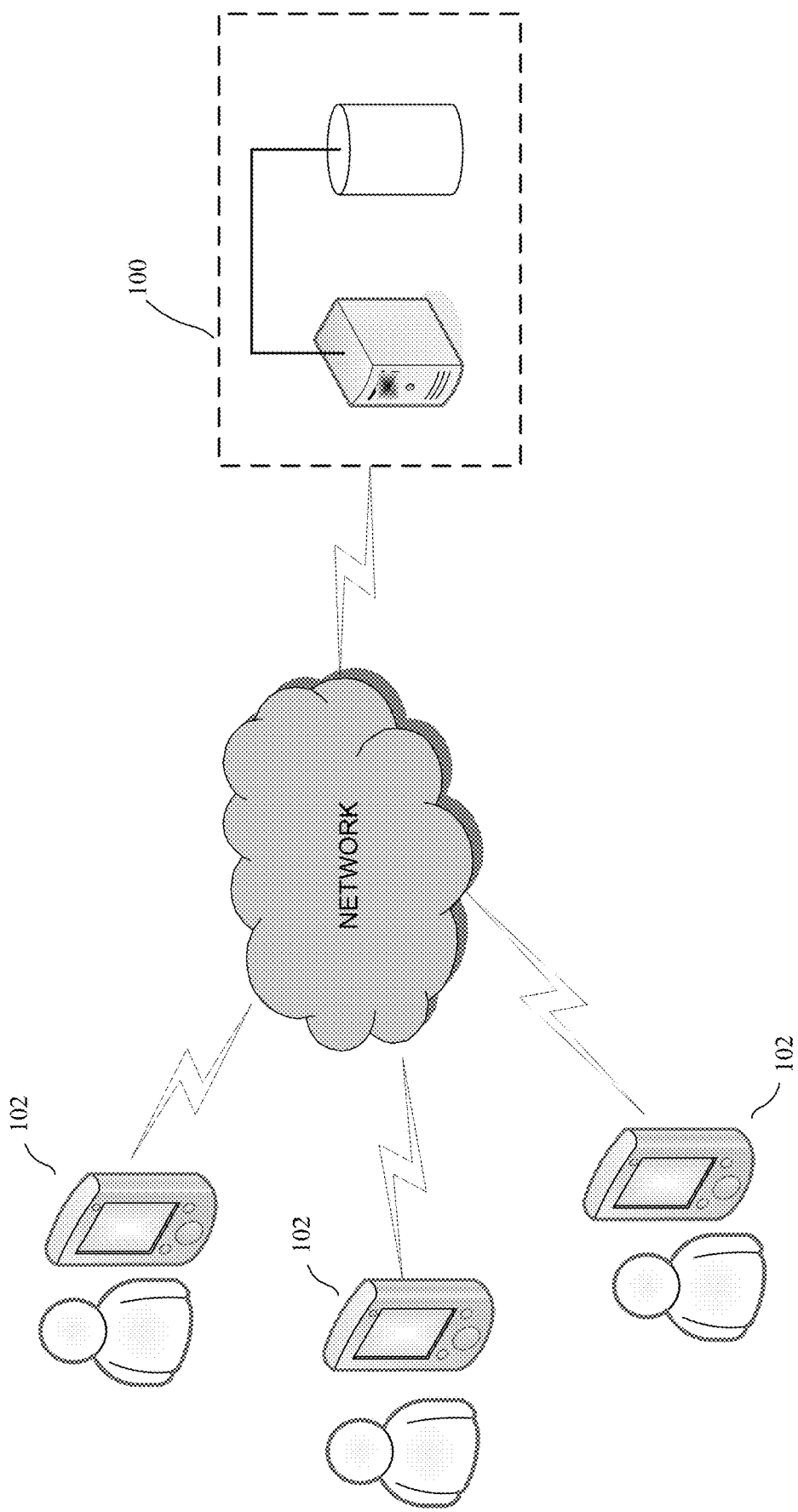
FIG. 1 illustrates an embodiment of a client/server based system to analyze a physiological state of nutrition and appetite and optimize nutritional intake.

A client/server based system to analyze a physiological state of nutrition and appetite, and the behavioral and attitudinal states of an individual and optimize nutritional intake according to an illustrative embodiment of the disclosure is described with reference to FIG. 1. The method and apparatus to monitor and analyze a physiological state of nutrition and appetite and optimize nutritional intake may include a computer based system 100.

The computer based system 100 in the illustrative embodiment includes one or more server computers, a network interconnecting the server computer(s) or data processing device(s) with one or more databases, and one or more electronic communication or client devices that can access, provide, transmit, receive, and modify information over the wired or wireless network. The computer based system 100 is in communication with a client device 102 of one or more user's/client's. The client device(s) 102 may be continually or periodically connected to the computer based system 100 or separate/disconnected from the computer based system 100. The client device(s) 102 may be an electronic communication device such as but not limited to a computer, personal digital assistant (PDA), cellular or mobile phone, and other devices that can access, provide, transmit, receive, and modify information over wired or wireless networks. The network may be a local area network or a wide area network and may be a private or public network of any size or scope. In an illustrative embodiment, the network is the Internet.

The computer based system 100, further described with reference to FIG. 2, may receive input data 200 from a user through the client device 102, from which the computer based system 100 may create a profile of the user. The input data 200 may include information about the user's physical characteristics, such as but not limited to age, sex, height, weight, body mass index, and other physical characteristics. The input data 200 may include other information about the user, such as but not limited to name and address. The input data 200 may include information about the user's physiological characteristics, such as but not limited to blood sugar level; heart rate; electrical activity; temperature; electrolyte level; oxygen level; endogenous upper digestive feedback signals that normally regulate eating such as ghrelin, cholecystokinin, leptin, insulin, glucagon, and amylin; and other physiological characteristics. The input data

200 may include information about the user's food preferences and/or avoidances, allergies, amount and timing of food consumption, carbohydrate intake, caloric intake, exercise activity, attitude, behavior, hunger levels, and other input data of the type. The input data 200 may include information about the user's health and nutrition goals, such as but not limited to the user's long term and short term weight loss/weight gain goals. The input data 200 may include information about the type of nutrition and appetite plan the user may desire to follow. The input data 200 may include personal information about the user such as but not limited to the user's religion, whether the user is a vegan or vegetarian, a personal calendar including dates and/or times of travel, vacations, events, parties, relationships, events and other personal information of the type. Input data 200 may also include links or other electronic means of deriving or gathering information from a user including the user's calendar, the user's social networking sites, the user's twitter account or other systems or processes that will generate relevant data about a user pertinent to the system and method according to the invention. For example, the computer based system 100 may be configured to automatically sync with the user's outlook calendar, electronic mail, or other similar system to determine social events that involve food consumption, travel or other activities.

Further, the input data 200 may include regular real-time information, which the computer based system 100 may use to update and/or monitor the progress of the user throughout the user's program. Such regular input data 200 may include any of the above mentioned information/data. The regular input data 200 may be received or collected by the computer based system 100 routinely in real-time, for example 1-3, 1-5, or 1-10 times daily, and/or monthly. Further, the system may decide it requires more information in which case and output message will be sent to the user via Output 224 which will engender more inputs to 200.

The computer based system 100 may receive or collect the input data 200 via the client device 102 through the use of a client/user interface, such as an interface installed on the client device 102, a phone application, and/or a remotely accessible interface. The user interface may include visual, audio, graphics, charts, and other features of the type. The user interface may include a menu incorporating a number of specific questions the user may answer, for example by typed, stylus/touch-screen, oral, and/or written. The user interface may include a menu incorporating a number of selection boxes and/or drop-down menus in which the user selects the correct answer to a number of specific questions. The user interface may include a prompt that prompts the user to key in or type the input data 200 into the computer based system 100 via the client device 102, wherein the user may be prompted via the client device 102 to input real-time input data 200 throughout one or more days. The user interface may include a selectively cascading input mechanism for selecting and/or rating the user's personal nutrition and appetite related activities, attitude, hunger, and other parameters.

Additionally, the computer based system 100 may receive or collect the input data 200 through biological/electronic monitoring systems, such as but not limited to electronic scales, pedometers, heart rate monitors, blood testing instruments, blood pressure monitors, invasive or non-invasive telemetry systems and other biological monitoring systems of the type.

The computer based system 100 may receive the input data 200 via the client device 102 and create an individual user profile 202. The individual user profile 202 may be stored in a database which may be integrated into the computer based system 100 and/or linked to the computer based system 100 through the wired or wireless network. In an illustrative embodiment, the individual user profile 202 is created when the user sets up the user's account.

The individual user profile 202 may hold a running/real-time profile on the user. The individual user profile 202 may include user input data 200, information relating to the user's current metabolic state and condition; motivational state and condition; nutrition plan phase; appetite cycle; consumption model; baseline biology; baseline metabolism; advanced metabolism; weight goals; adjusted weight goals; distance from goals; historical user data, such as user input messages and output messages; and other information of the type. The individual user profile 202 may also track the time and date the user input each portion of the user input data 200, and of the output messages sent to the user via the client device 102.

Further, the individual user profile 202 may be used to issue reports based on the user's state and/or progress. The individual user profile 202 may also be linked to third parties, such as for example physicians, nutritionists, or other health care professionals, insurance companies, and other such parties of the type. However, in order for the individual user profile 202 to be available to third parties, the user may have to allow or grant the third party access to the individual user profile 202 and be in compliance with such Federal codes as HIPPA.

In the illustrative embodiment, the computer based system 100 includes exogenous data 204 and/or crowd data 206. The exogenous data 204 may be stored on a database which may be integrated into the computer based system 100 and/or linked to the computer based system 100 through the wired or wireless network. The exogenous data 204 may include personal information about the user such as but not limited to a personal calendar including dates and/or times of travel, vacations, events, parties, relationships, events and other personal information of the type. The exogenous data 204 may include country calendars, such as but not limited to the holidays and events celebrated throughout various countries. The exogenous data 204 may include religious calendars, such as but not limited to the religious holidays, religious events, and religious dates associated with various religions. The exogenous data 204 may include historical data. The exogenous data 204 may include other data, such as but not limited to the weather, news, stock market, events schedules of a particular town, city, and/or state, and other data of the type. The exogenous data may include information about an employer, about the user's wealth, relative wealth, and wealth relative to the user's community and investments and links to the user's social networks sites.

All or a portion of the exogenous data 204 may be input into the computer based system 100 by the user, obtained through the individual user profile 202, imported through the sync functionality with the user's outlook calendar, email, or other similar system, obtained through Extensible Markup Language (XML) feeds, and/or web crawlers or spiders configured to search the world wide web for relevant content. Further, all or a portion of the exogenous data 204 may be static data, for example the calendars; and/or data that may be updated periodically and/or continuously, such as through user input, live XML feeds and/or web crawlers.

The crowd data 206 may be stored on a database which may be integrated into the computer based system 100 and/or linked to the computer based system 100 through the wired or wireless network. The crowd data 206 may include all the data collected by the computer based system 100, especially but not limited to the progress and result information (for example, the trends, suggestions, reactions, and effectiveness) of past and/or present users or third party users of the computer based system 100. In an illustrative example, the crowd data 206 is the "progress reports" from individual users, i.e. information that allows the computer based system 100 to learn from the experience of many users whether the computer based system 100 provided an effective experience. The progress and result information of individual users may be used to modify the decision rules, for example by altering or disposing of rules that are less effective. The crowd data 206 may be static data and/or data that is updated periodically and/or continuously, such as through sync functionality with all the data, including the user's data, incorporated into the computer based system 100. The crowd data may be stored as a signature or condensed profile to summarize the result of data mining processes to lessen the computational intensity to determine the relevance of the crowd data to the user.

The computer based system 100 may utilize the crowd data 206 to analyze how third party users have or are reacting to the third party users' specific nutrition regimens and incorporate the information into the current user's nutrition regimen to make the user's nutrition regimen more effective. In an illustrative embodiment, the crowd data 206 is run through a machine learning algorithm and generalized. These types of learning systems generally include decision trees, Bayesian Learning Networks, Markov Models, Support Vectors, Gaussian Mixture models, and/or regression systems used to weigh the most relevant user data against the crowd data 206. More particularly, the crowd data 206 is taken into a data base classified across a number of different parameters related to profile, goals, diet where profile includes a progress tracker. Using the machine learning techniques including the Gaussian classifiers, decision trees, neural networks, Bayesian networks, Markov models and other similar techniques, signatures for the successes of different instances of templates against different profiles including the impact of different types of external and data are created. This integration is used to help more accurately predict what will work for like individuals and understand the impact of certain external factors.

Basically, the computer based system 100 instantiates rules in what is perceived to be the 'correct' manner, for example, when and in what form a message is sent to make it more likely that the user will follow the instruction of the message. In an illustrative embodiment, the computer based system follows a "do ask and do tell" policy. For example, the computer based system 100 queries the user on both what is eaten, and when; and further, how the user is doing vis-à-vis satiety and weight loss. In such fashion, the computer based system 100 can grade itself on both fronts (rules and method). The evaluation is first and foremost applied to the individual user. Basically, the computer based system 100 wants to know did the user comprehend the message, did the user follow instructions, was following the instruction effective, both in terms of: how did the user feel (in the appropriate time window) after following the instruction (or not) and how is the user's nutrition regimen progressing.

These grades and assessments can be sent to a central repository where macro phenomena can be examined, for example: "Rule stating 'drinking water 2 hours before dinner increases satiety and fullness' was adhered to but user reported low levels of satiety". This may transmit in the form "rule 17; compliance 9; efficacy 3"). If a rule seems to be working only 20% of the time, as seen in this example, instruction may be sent to the individual user's nutrition and appetite plan and methodology to tweak the rule, either to remove it entirely, or to have a low threshold to remove it, if it is showing early signs of failure.

In the illustrative embodiment, the computer based system 100 includes an aggregate profile 208. The aggregate profile 208 may include the individual user profile 202 integrated with the crowd data 206 and the 204 exogenous data. The aggregate profile 208 may be used by the computer based system 100 to modify, change, and/or update the user's nutrition regimen. The aggregate profile 208 may be stored on a database which may be integrated into the computer based system 100 and/or linked to the computer based system 100 through the wired or wireless network. Generally, the aggregate profile 208 is a profile that is generated by integrating the individual user profile 202, exogenous data 204, and crowd data 206 together. In an illustrative embodiment, the aggregate profile 208 is created by integrating the individual user profile 202, exogenous data 204, and crowd data 206 together through a machine learning algorithm. These types of learning systems generally include decision trees, Bayesian Learning Networks, Markov Models, Support Vectors, Gaussian Mixture models, and/or regression systems used to weigh the most relevant user data against the crowd data 206 to determine signatures for the successes of different instances of templates against different profiles including the impact of different types of external data. This integration is used to help more accurately predict what will work for like individuals and understand the impact of certain external factors.

In the illustrative embodiment, the computer based system 100 includes nutrition regimen template data 210. The nutrition regimen template data 210 may be stored on a database which may be integrated into the computer based system 100 and/or linked to the computer based system 100 through the wired or wireless network. The nutrition regimen template data 210 may include templates of known diet programs and/or nutrition regimens, such as but not limited to nutrition regimens based on portion control and conservation, body building, metabolic changes, food types, food choices or mixes, exhaustion and boredom, appetite suppression, the glycemic index approach, exercise, protein consumption, calorie counting, philosophies (for example: vegan, halal, kosher, allergies, and aversions), and other diet programs or nutrition regimens of the type. The nutrition regimen template data 210 may be customizable and/or parameterizable to any diet or nutrition and appetite philosophy and user based on the individual user's input data 200 and individual user profile 202, such as the user's goals. The diet programs and nutrition regimens may also be customizable to allow the learning system to modify the 212 nutrition and behavior rules to be modifiable based on the efficacy of those rules against the 202 individual user profile without changing the immutable aspect of the nutrition regimen.

In the illustrative embodiment, the computer based system 100 includes a nutrition engine 212. The nutrition engine 212 may be a module, processor, or program which may be integrated into the computer based system 100 and/or linked to the computer based system 100 through the wired or wireless network. The nutrition engine 212 may be in communication with a decision engine 214, the nutrition regimen template data 210, scientific data and/or rules 216, and a learning process 218, all discussed in greater detail hereinafter. The nutrition engine 212 may receive the nutrition regimen template data 210, and the user's input data 200 and profile 202 through the decision engine 214. The nutrition engine 212 may integrate the nutrition regimen template data 210, and user's input data 200 and individual user profile 202 to create a customized and/or parameterized nutrition and appetite plan for the user. The nutrition engine 212 may be customized and/or parameterized, for example based on the nutrition strategy, modality, type, phase, goals, time management, and food choices. Goals, may include but are not limited to the goals of aligning eating habits with appetite, eating ahead of appetite, eating smaller and more frequent meals, eating protein (and not simple sugars) to suppress rebound hunger, lose weight, lose weight to obtain a target weight, build muscle, calorie monitoring, and carbohydrate monitoring.

The nutrition engine 212 may further receive scientific data and/or rules 216, which may be held in a database which may be integrated into the computer based system 100 and/or linked to the computer based system 100 through the wired or wireless network. The nutrition engine 212 may integrate the scientific data and/or rules 216, with the nutrition regimen template data 210, and user's input data 200 and individual user profile 202 to create the most effective nutrition and appetite plan and/or regimen in terms of nutrition and behavior rules for the user.

The scientific data and/or rules 216 may include data and/or rules such as but not limited to food index listings containing calorie count, glycemic index, satiation potential, metabolic effects, roughage, and other nutritional information for all available comestibles. In an illustrative embodiment, nutrition regimens are produced by the application of individual parameters to nutrition regimen templates. A nutrition regimen is informed by a philosophy (for example an "on-one-leg description", a "high protein" and/or "all grapefruit") of the nutrition regimen and this philosophy is manifest in a set of rules 216. That rule set 216 is then instantiated for the particular individual user, yielding a specific set of prescribed and proscribed foodstuffs (conceptually, a pantry) and a plan for consumption (sample menus). The specific individual user parameters passed to the nutrition regimen include, by way of example, some of the following: gender, age, body mass index, baseline daily energy consumption, current weight, target weight and food allergies/aversions. Taken together, the nutrition rules and the individual parameters produce sample menus, using only foods in the "pantry."

In an illustrative example, the nutrition regimen is based on a philosophy for a "low carbohydrate diet." In the low carbohydrate diet the general "science" rules 216 may include, but are not limited to: limit complex carbohydrate consumption, 4 Kcal/gram, to 30% of total caloric intake, with protein (also 4 Kcal/gram) targeted at 40% and fat (9 Kcal/gram) at 30% and limit total caloric intake to 90% of baseline daily energy consumption. Parameters based on age and BMI produce the calculated baseline daily energy consumption (in Kcal); 90% of that is the target daily intake (TDI). The diet is then set: TDI*0.3/4 defines the number of grams of complex carbohydrates, TDI*0.4/4 defines the number of grams of protein, and TDI*0.3/9 defines the number of grams of fat. Sample menus are then created, with serving sizes of particular foods satisfying the (mathematical) constraints. The selected foods are modified further by template parameters that note likes/dislikes/aversions, etc—for example, 35 grams of protein can be chosen from 5 ounces of steak or salmon, but users who are allergic to fish won't get offered salmon.

The parameterization of the nutrition regimen allows the system to substitute and modify like food types, occurrences, sequences to adapt to increase progress or for non-planned events like going to a restaurant instead of eating a prepared meal.

Figure 3:
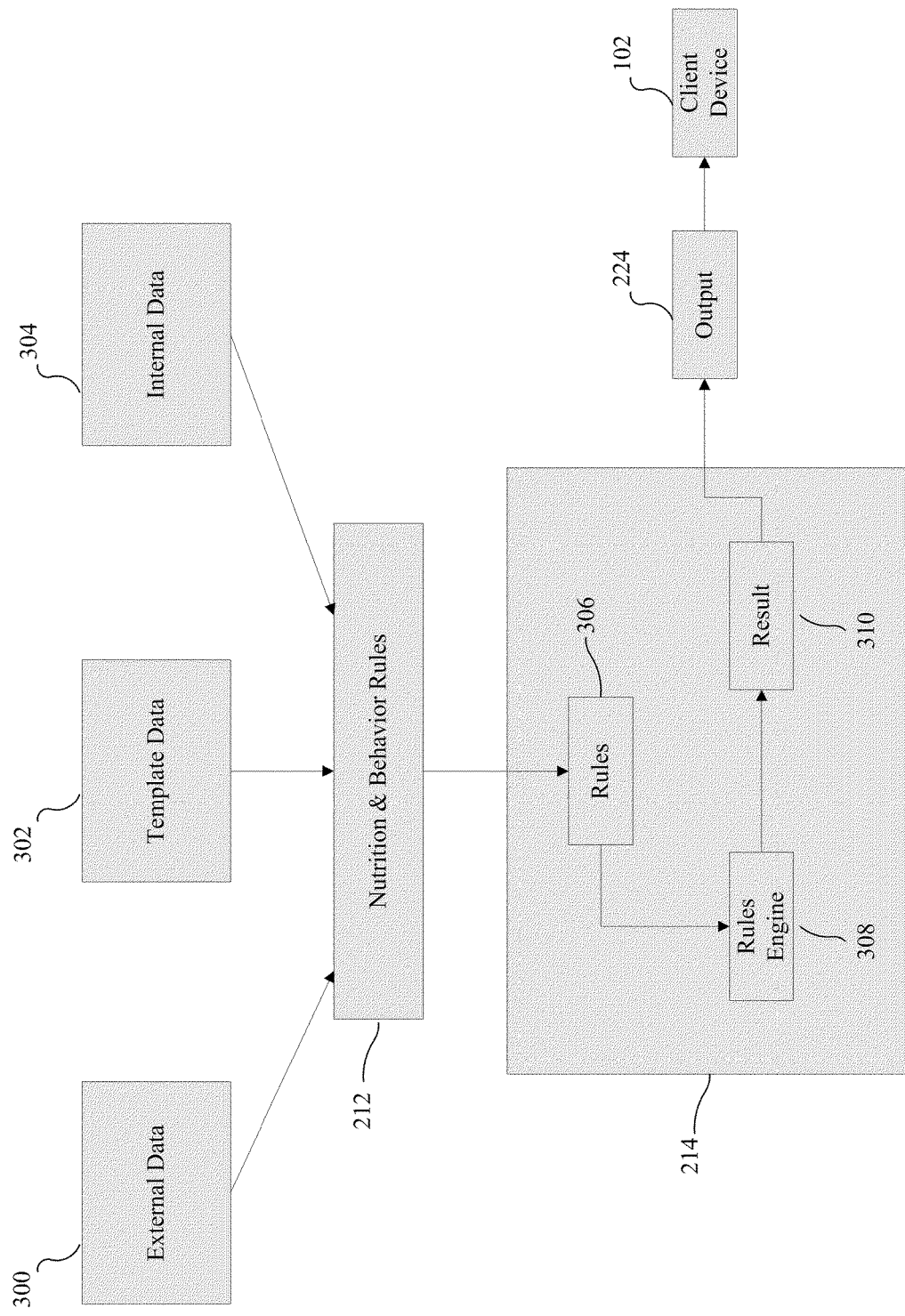
FIG. 3 illustrates a block diagram of the relationship and functionality between the decision engine and the nutrition engine of the computer based system.

A block diagram of the relationship and functionality between the decision engine and the nutrition engine according to an illustrative embodiment is described with reference to FIG. 3. In this illustrative embodiment, the nutrition engine 212 communicates with the decision engine 214 to compile external data 300, template data 302, and internal data 304. The external data 300 is information from the individual user profile 202, the exogenous data 204, and/or the crowd data 206, such as for example information relating to date, user's location, temperature, time, and other such parameters of the type. The template data 302 is information from the nutrition regimen template data 210 and is based on the user's nutrition and appetite plan or regimen (i.e. the type of diet), such as for example the types and portion sizes of food the user is to consume. The internal data 304 is information from the individual user profile 202, such as for example information relating to the user's physiology, history, profile, and relationship.

As an illustrative example, the external data 300 communicates to the nutrition engine 212 that it is 11:00 am on Monday. The template data 302 communicates to the nutrition engine 212 that the user is to consume three ounces of fish, specifically tuna or salmon, for lunch on Monday. The internal data 304 communicates to the nutrition engine 212 that the user has not consumed fish recently and that the user enjoys tuna. The nutrition engine 212 may then compile the information and communicate the information to the decision engine 214, where the decision engine 214 determines a message to send to the user's client device 102, for example that the user is to consume three ounces of tuna for lunch today.

It should be appreciated that the above example is merely an illustration of one process. The message and/or output sent to the user via the client device 102 will likely be different based on any number of different combinations of information.

In the illustrative embodiment, the computer based system 100 includes a satiety meter 220. The satiety meter 220 may be a module, processor, or program which may be integrated into the computer based system 100 and/or linked to the computer based system 100 through the wired or wireless network. The satiety meter 220 may be in communication with the scientific data and/or rules 216, and the decision engine 214. The satiety meter 220 may receive the user input data 200 and individual user profile 202, such as the user's physiological information from the decision engine 214. The satiety meter 220 may analyze the user input data 200 and individual user profile 202 and establish baseline states of the user including nutrition, hunger and other relevant information to calculate satiety. For example, the baseline nutritional state may be determined by assessing fasting versus feasting nutritional states, averaging nutritional states of the user over a period of time, and using a generic model of human metabolism. Establishment of the baseline nutritional state may allow the computer based system 100 to adapt to the unique nutritional physiology of a given user, which is an important aspect because nutritional physiology varies significantly with a number of factors including, but not limited to, body mass, gender, and age. Or the system may read the continuous output of a glucose monitor to determine a predictive model for user. Or the system may query the user multiple times a day and monitor when the user eats based on the inputs in order to create a predictive model of when the user will be hungry.

Figure 4:
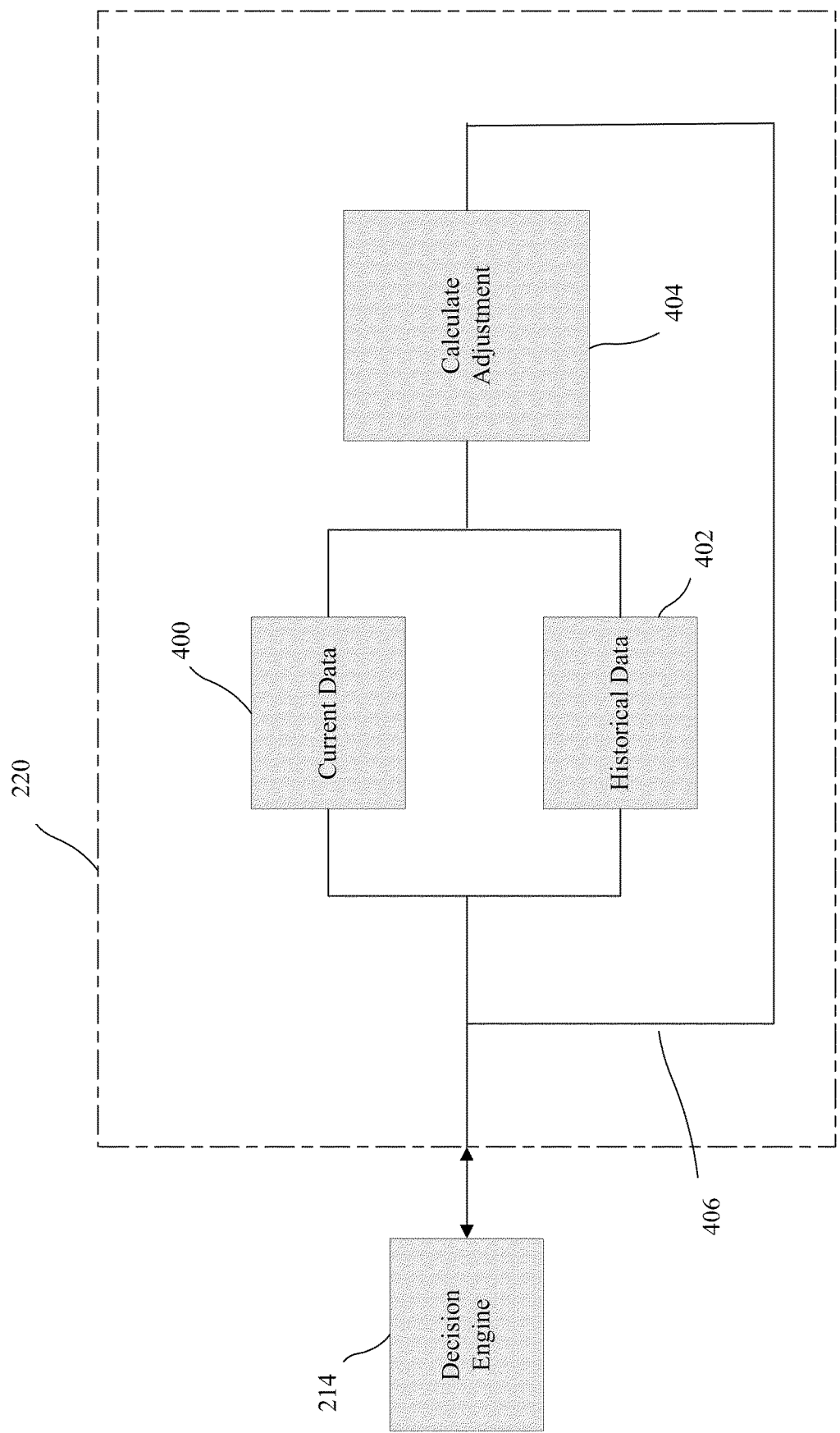
FIG. 4 illustrates a block diagram of an embodiment of a satiety meter of the computer based system.

A block diagram of an embodiment of a satiety meter according to an illustrative embodiment is described with reference to FIG. 4. As illustrated in FIG. 4, the satiety meter 220 may assay and monitor the user's profile 202 including the nutritional state 400 of the user based on the input data 200. This monitoring may be completed at designated time intervals, or in real time. The satiety meter 220 may compare the user's profile 202 including the nutritional state 400 of the user to historical nutritional states of the user 402 or the baseline nutritional state of the user and analyze the states, according to the scientific data and/or rules 216, to calculate a differential value 404. The differential value may be correlated with established goals to anticipate the nutritional needs of the user. The satiety meter 220 may then preemptively determine the appropriate nutritional intake of the user to prevent the onset of hunger and communicate the information to the decision engine 214.

The satiety meter 220 may implement a feedback loop 406 that may monitor the basic rhythm of hunger and attitude in a user at the physiological level over the course of time, and anticipate the onset of hunger (as a function of attitude) of the user by monitoring changes in nutrition and appetite related physiological cues. Thus, the satiety meter 220 may work in collaboration with the decision engine 214 to determine the types of foods and when the foods should be consumed by the user to prevent the user from experiencing the onset of hunger. Further, the satiety meter 220 may provide input to the decision engine 214 and message calculator 228 that contributes to the generation of food suggestion(s) or motivational messages 224 in the form of an output message to be sent to the user via the client device 102 informing the user of when and what to consume to prevent the onset of hunger, and/or to keep the user on track in accordance with the user's nutrition and appetite plan and/or regimen. While the satiety meter 220 is described above as a being integrated into the computer based system, it should be appreciated that the satiety meter 220 may be a separate system and function independently. It should be noted that the satiety meter is compatible with almost every type of nutrition regimen and rules instances of those nutrition regimens. Further the modeling of the satiety meter should be subject to basic 216 science rules and improved with the 218 learning system.

In the illustrative embodiment, the computer based system 100 includes a binge preventer 222. The binge preventer 222 may be a module, processor, or program which may be integrated into the computer based system 100 and/or linked to the computer based system 100 through the wired or wireless network. The binge preventer 222 may be in communication with the decision engine 214. The binge preventer 222 may receive the user's input data 200, individual user profile 202 and exogenous data 204 through the decision engine 214 and may analyze and monitor such data to determine when a user has and/or may experience a situation where the user may be tempted to binge or tempted to stray from the user's nutrition and appetite plan and/or regimen and communicate that information to the decision engine 214. The binge preventer 222 may determine when a user has engaged in a binge and communicate with the decision engine 214 to adjust the user's nutrition and appetite plan and/or regimen to correct or compensate for such activity. Further the binge preventer 222 may communicate with the decision engine 214 and message calculator 228 to generate motivational messages 224 in the form of an output message to be sent to the user via the client device 102 to give positive reinforcement to the user to prevent the user from engaging in a binge or repair a binge if the user falls off of the user's nutrition and appetite plan and/or regimen. The positive reinforcement is important because by setting up a notion that nutrition regimens are not about good and bad actions, the emotional and intellectual behavior binges should not create the guilt associations that happen with normal diets. The binge preventer rules or logic may also be updated by the 218 learning system.

Figure 5:
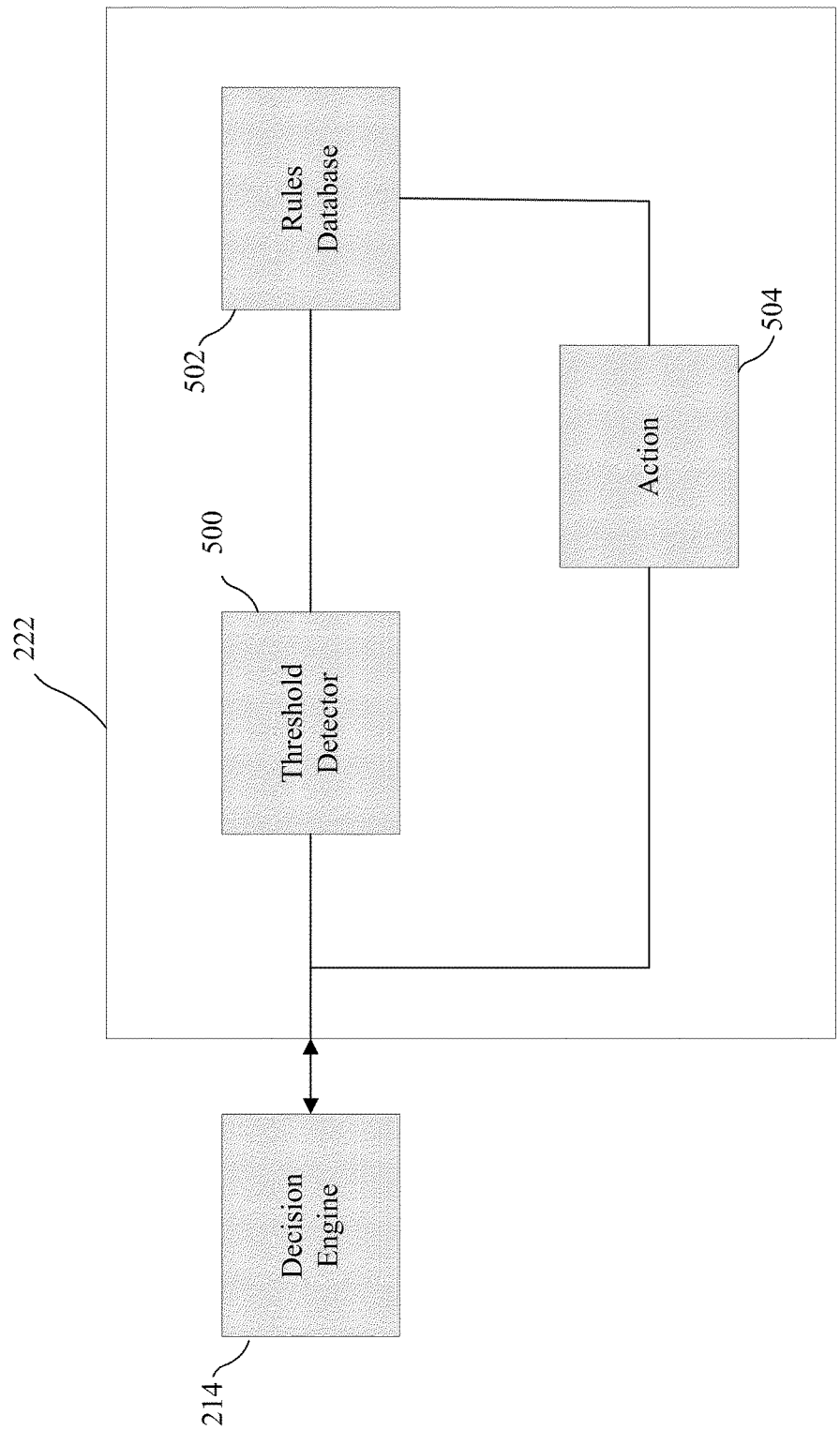
FIG. 5 illustrates a block diagram of an embodiment of a binge preventer of the computer based system.

A block diagram of a binge preventer of the computer based system according to an illustrative embodiment is described with reference to FIG. 5. The binge preventer 222 monitors the user via information from the individual user profile 202 and the exogenous data 204. The binge preventer works across all diet instances (i.e. is diet template "agnostic"). The binge preventer monitors, and in extreme cases the binge preventer 222 is implemented as needed. The binge preventer 222 includes a threshold detector 500, a rules database 502, and an action process 504. The threshold detector receives information from the individual user profile 202 and the exogenous data 204, and analyzes and monitors the information received to determine when a user has and/or may experience a situation where the user may be tempted to binge or tempted to stray from the user's nutrition and appetite plan and/or regimen. If the threshold detector 500 determines that the user has and/or may experience a situation where the user may be tempted to binge or tempted to stray from the user's nutrition and appetite plan and/or regimen based on the information received, the threshold detector 500 communicates that information to the rules database 502, which then communicates with the action process 504. The action process 504 analyzes the rules, which may represent a series of If-Then rules based on thresholds set for the user with respect to user input and/or exogenous data, and determines whether to implement an action in extreme cases, for example, to prompt the decision engine 214 to communicate an output message to the user via the client device 102 to motivate the user to stay on track with the user's nutrition and appetite plan and/or regimen and/or prevent the user from engaging in a certain course of action. The logic of the binge engine is not limited to a rule based system but any other mechanism capable of storing a logical calculation or inference system. While the binge preventer 222 is described above as a being integrated into the computer based system, it should be appreciated that the binge preventer 222 may be a separate system and function independently.

In the illustrative embodiment, the decision engine 214 is included in the computer based system 100. The decision engine 214 may be a module, processor, or program which may be integrated into the computer based system 100 and/or linked to the computer based system 100 through the wired or wireless network. The decision engine 214 may continuously update, analyze and/or monitor the individual user's profile 202, the user's customized and/or parameterized nutrition and appetite plan and/or regimen based on the nutrition engine 212, the user's nutrition and appetite strategy, and/or the user's relevant behavior based on the user's input 204 and provide output 224 to the user via the client device 102, such as feedback, recommendations, suggestions and messages. Message delivery may be employed to continuously motivate and guide the user's behavior to optimize the effectiveness of the nutrition and appetite strategies. The decision engine 214 may provide food consumption strategies to prevent hunger, binging behavior and anticipate circumstances that often lead to the failure of nutrition and appetite plans. Messages can be delivered to the user via the client device 102 as emails, visuals guides, audio messages and eventually maybe as the direct delivery of nutrient and simuli. Messages can include instruction to consume certain food, queries for the nutrition and appetite plan's current state, and motivational messages to provide positive and negative feedback. Thus, the computer based system 100 may be a two way system for collecting the user's nutrition and appetite related activities and attitude and distributing customized behavioral messages as output 224 over a communications network to optimize adherence to a diet or nutrition and appetite plan.

Figure 2:
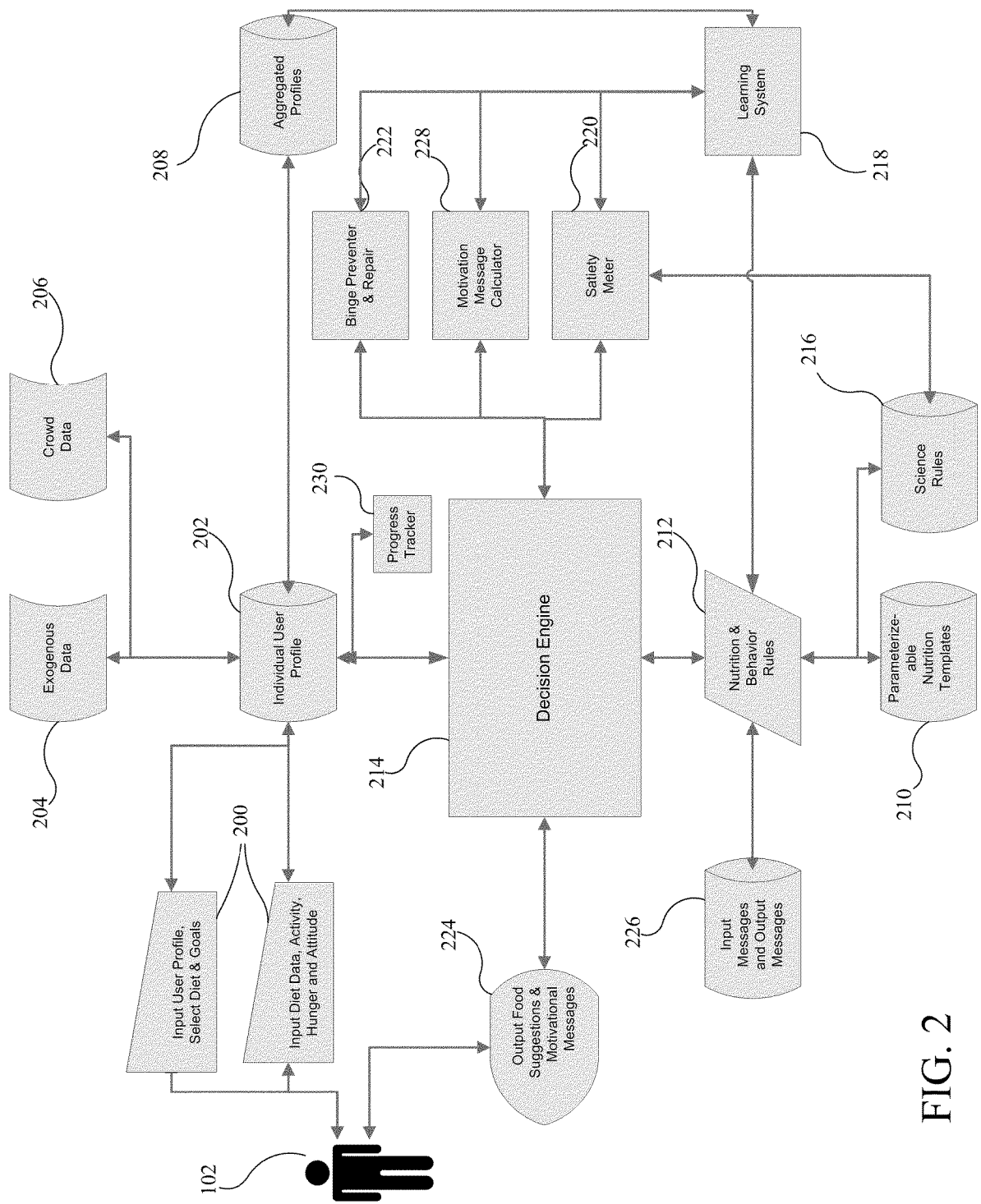
FIG. 2 illustrates a block diagram of an embodiment of a computer based system to analyze a physiological state of nutrition and appetite and optimize nutritional intake.

As illustrated in FIG. 2, the decision engine 214 may receive data and/or information communicated or transmitted from the user's input data 200 via the client device 102, the individual user's profile 202, the binge preventer 222, the satiety meter 220, the nutrition engine 212, nutrition regimen template data 210, scientific data and/or rules 216, exogenous data 204, and/or crowd data 206. The decision engine 214 may compile the information received and determine the next course of action the user should take as a function of the information received, the state of the user's nutrition and appetite plan and the rules of the user's nutrition and appetite plan (i.e. diet template), such as what to consume, when to consume, and/or transmit recommendations, suggestions, and motivational messages to the user as output 224 via the client device 102, wherein the output 224 may be sent to the client device 102 through the user interface.

In the illustrative embodiment, referring still to FIG. 2, a progress tracker 230 may be included in the computer based system 100. The progress tracker 230 may be a module, processor, or program which may be integrated into the computer based system 100 and/or linked to the computer based system 100 through the wired or wireless network. The progress tracker 230 may receive user input data 200 from the decision engine 214 and track the weight and nutritional status of the user over time. It is well known in the art that the nutritional status of an individual is not given solely by the user's parameters at an instant but rather over the course of these parameter's variation over time, for example, a 90 kg person who has never lost weight is physiologically different than a 90 kg person who is down from 110 kg over the last 3 months. The latter represents a monthly loss of approximately 6% of body mass, and will provoke an "anti-starving" physiological response. Thus, the progress tracker, to measure where the user is going needs a representation of where the user came from.

Most sophisticated eating regimens include multiple phases with a minimum usually being an intense period of establishing rules and then a maintenance period. For instance, in the Atkins Diet there are four phases which are induction, ongoing, pre-maintenance and maintenance. Usually the greatest progress is made during the initial period and then foods are gradually added back into the diet regimen when some of the goals are realized. Transition from one phase to another is usually only based on weight goals and is often lost in the next cycle as the user and the diet haven't properly adapted. And even a four phase approach is only a crude approximation of the changes in the user's biology and metabolism; hence in the system and method according to the invention progress is "tracked" continuously and instantaneously and includes a large number of other factors beyond weight.

The progress tracker 230 not only measures the individual's progress against the user's initial goals and moves the individual through phases of the nutrition regimen, but monitors the user's progress against other goals, for example emotional connection to food, behavior at parties and events. Additionally, as experience is gained the nutrition regimen evolves to best suit the individual during the particular circumstance of the user's life and the world around the user. The progress tracker 230 is also a user output cue to indicate the user's success not just in accomplishing weight-loss but in adhering to the outlined nutrition regimen. The progress tracker 230 also provides feedback to the user through the decision engine 214 in the form of output suggestions/messages 224, such as, but not limited to accolades acknowledging success with regard to avoiding a certain food or drink at an event, or accolades on progressing a day without failing. These incremental positive messages focus on behavior as well as accomplishments in the context of an adapted nutrition and behavior regimen.

Referring back to FIG. 3, the decision engine 214 implements core rules, and in this illustrative embodiment comprises rules 306, a rules engine 308, and results 310. In the embodiment illustrated in FIG. 3, the decision engine 214 communicates with the nutrition engine 212, as discussed above. The decision engine 214 receives information from the nutrition engine 212 and applies rules 306 to the information received. The rules engine 308 then processes the information and rules to determine a result 310. The result 310 may include output 224 to be communicated to the user via the client device 102. The result 310 may include a next action selected from a table of next actions, such as a query to send an output 224 message to the client device 102. As an example, the result 310 includes a query to prompt a motivational message to be sent to the user via the client device 102 as output 224 instructing the user to consume a specific amount of a type of food.

The output 224 may be in the form of a written message, an audio message, or a visual message or display. Visual messages and/or displays may include but are not limited to graphs, charts, changing shapes/sizes of icons of body parts, icons of characters, self image views, counters that count up and/or down, food cues, and food portion cues. The output 224 may incorporate aspects of a video game, such as levels the user may progress to and/or unlock based on the user's progress and to provide secondary positive reinforcement.

The output 224 messages to be sent to the user, via the client device 102, by the decision engine 214 may include messages 226 held in a database which may be integrated into the computer based system 100 and/or linked to the computer based system 100 through the wired or wireless network. The messages 226 may include numerous types of messages, such as but not limited to motivational messages, query messages, transactional messages, the output of nutrients, recommendations of the type of food to consume, recommendations of when to consume food, messages relating to exercise, and other messages of the type which may include messages to other devices including but not limited to exercise machines, blenders and smart refrigerators.

In the illustrative embodiment, the computer based system 100 includes a motivation message calculator 228. The motivation message calculator 228 may be a module, processor, or program which may be integrated into the computer based system 100 and/or linked to the computer based system 100 through the wired or wireless network. Illustratively, the motivation message calculator 228 is nutrition and appetite plan agnostic. The motivation message calculator 228, in communication with the decision engine 214, may analyze the user's current nutrition and appetite plan state and behavioral and attitudinal state and calculate and/or determine the output 224 message to be sent to the user from an output message database 226 or table, via the client device 102, to encourage the user to stay on track and/or prevent the user from engaging in a certain course of action or encourage the user to engage in a course of action. The message calculator 228 may incorporate the science of psychology and/or results of third party data to formulate or select a message to the user or to determine the appropriate time and sequence of one or more messages. The motivation message calculator 228 may filter the message through a psychology filter to ensure the message is maximally motivational.

The motivation message calculator 228 may create new messages based on user and third party data, such as past reactions to messages as determined through the learning system 218. The motivation message calculator 228 may consider boredom, social signaling and other non-nutritional aspects of food when determining and/or choosing an output 224. The motivation message calculator 228 may customize messages to the user based on message inputs or input data 200 from the user, the individual user profile 202, the decision engine 214, nutrition and appetite strategies, exogenous data 204, and crowd data 206. For example, the exogenous data 204 may be used to navigate circumstances that might be salient for properly maintaining dietary behavior including holidays, business and personal schedules, temperature, activity and exogenous events. While the motivation message calculator 228 is described above as a being integrated into the computer based system, it should be appreciated that the message calculator 228 may be a separate system and function independently.

Figure 6:
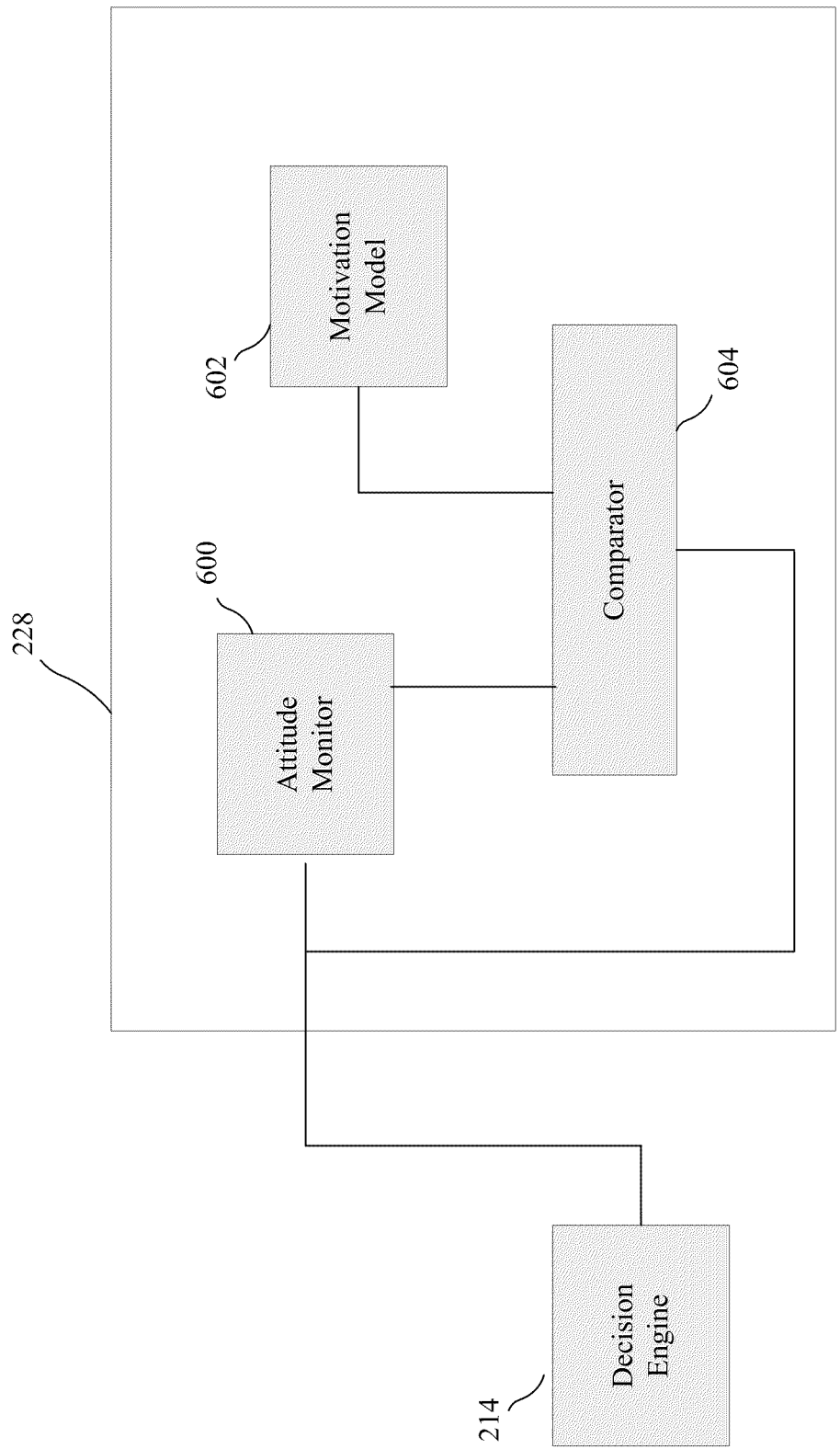
FIG. 6 illustrates a block diagram of an embodiment of a motivation system and message calculator of the computer based system.

A block diagram of a motivation message calculator of the computer based system according to an illustrative embodiment is described with reference to FIG. 6. As illustrated in FIG. 6, the message calculator 228 includes an attitude monitor 600, a motivation model 602, and a comparator 604. In this illustrative embodiment the message calculator 228 may address the will of a user, the user's emotions, and directions provided to the user to provide positive motivational messages to the user. The attitude monitor 600 monitors the user's attitude based on the input 200, the individual user profile 202, exogenous data 204, and the crowd data 206. The motivation model 602 is designed to converge will, emotion, and path (the regimen) in accordance with the user's nutrition and appetite plan, and modern behavioral science. The attitude monitor 600 and motivation model 602 communicate with the comparator 604. The comparator 604 compares the user's attitude (will and emotion), based on information from the attitude monitor 600, to the information from the motivation model 602 to determine whether the user is diverging, will diverge, or has diverged from the user's nutrition and appetite plan. As an example, will may be an instantaneous vector corresponding to the direction and magnitude, and the emotion an instantaneous vector corresponding to will and emotion for the same direction. The comparator 604 compiles the vectors and determines a divergence level from the proper path. If the divergence level is greater than a safe level the comparator supplements the next action, corresponding to the decision engine 214, with a motivational message. Additionally, the message calculator 228 may prompt the decision to query the user via the client device 102 through the output 224 and input 200 to determine the user's current attitude. One aspect of the motivation message calculator is to query the user to motivate for more inputs for example reminding the user to input the user's attitude in the morning.

Figure 7:
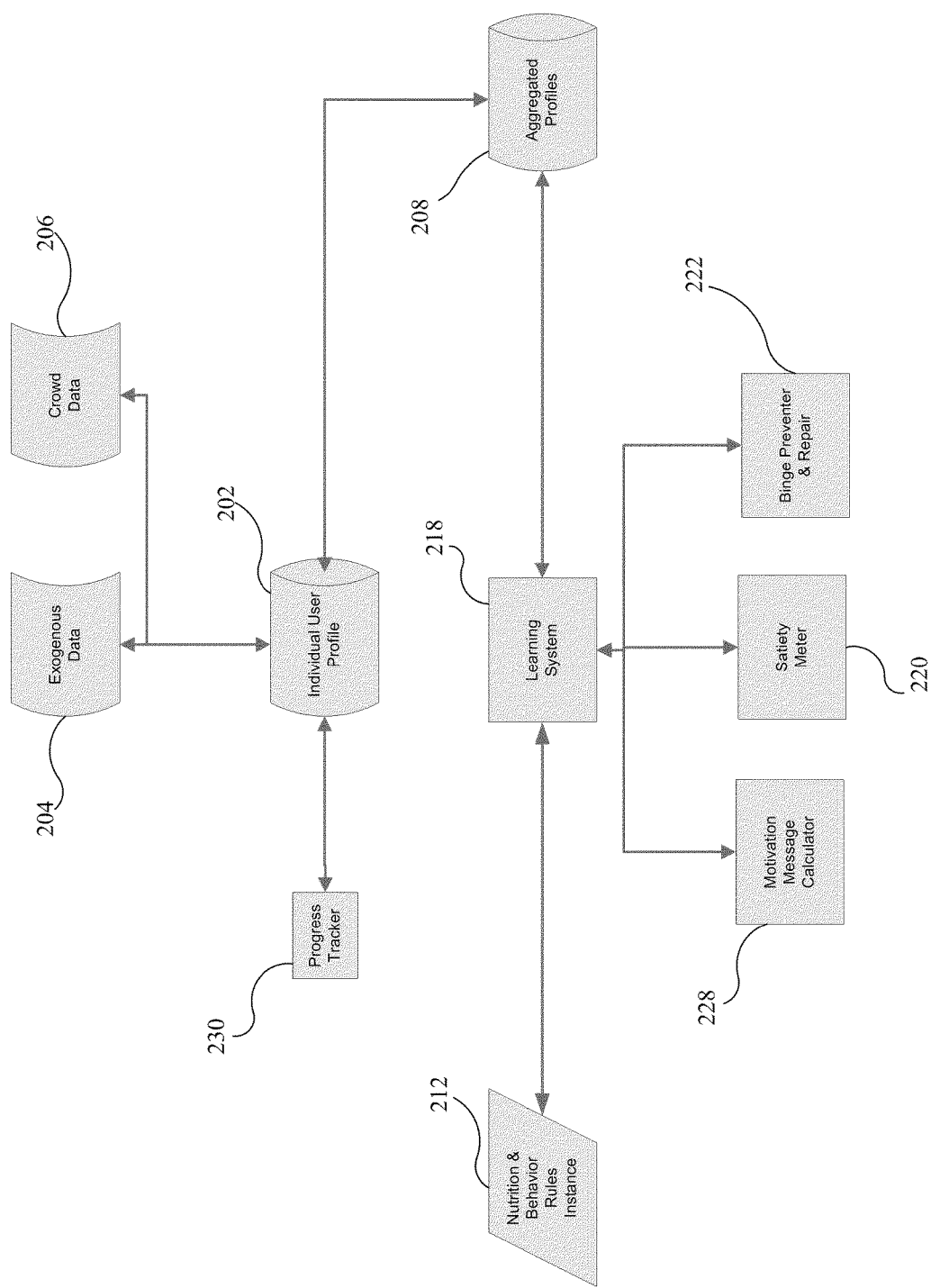
FIG. 7 illustrates a block diagram of an embodiment of a learning process in the context of the computer based system.

In the illustrative embodiment, the computer based system 100 includes a learning process 218. The learning process 218 may be a module, processor, or program which may be integrated into the computer based system 100 and/or linked to the computer based system 100 through the wired or wireless network. A block diagram of a learning process implemented in the computer based system according to an embodiment is described with reference to FIG. 7. As illustrated in FIG. 7, the learning process 218 may receive the user's input data 200, individual user profile 202, exogenous data 204, crowd data 206, information from the progress tracker 230, and the aggregated profile 208. The learning process 218 may monitor, assay, and/or analyze the user's input data 200, individual user profile 202, exogenous data 204, crowd data 206, progress tracker 230, and aggregated profile 208 to determine ways to enhance the user's nutrition and appetite plan and/or regimen. The learning process 218 may communicate with the nutrition engine 212, the message calculator 228, satiety meter 220, and the binge preventer 222; and may modify and/or update the parameters of the user's nutrition and appetite plan based on the progress and/or adaption of the user to the nutrition and appetite plan. For example, the learning process 218 may modify the parameters of the nutrition engine 212, and/or the decision engine 214 to optimize the user's nutrition and appetite plan, and/or update the user's profile or progress. Thus, the computer based system 100 can learn and improve the user's nutrition and appetite strategy based on the user's response to the output 224 and that of other users' similar experience based on the crowd data 206.

The learning process 218 may employ classical machine learning models and other learning models such as for example, Supervised learning, Unsupervised learning, Semi-supervised learning, Reinforcement learning, Transduction, and other learning models of the type. In this illustrative embodiment, the learning process 218 classifies the successes and failures of the sum of the aggregate profiles 208 against the next actions of the decision engine 214, exogenous data 204, the nutrition and appetite plans, satiety meter and the motivational messages from the motivation message calculator 228 and decision engine 214. The learning process 218 then generates updates, such as nutrition and appetite plans or modifications thereto, motivation types, and output 224 types (such as audio, textual, and/or video type outputs to the user via the client device 102) based on the successes and failures of the sum of the aggregate profiles 208.

The learning process 218 also exchanges information with one or more individual user profiles 202 to classify and determine and/or learn the effects of users' exogenous data 204, such as holidays, weather, personnel, travel, work, etc. The learning process 218 then determines preventative actions and/or cures based on the effects of users' exogenous data 204. As an example, the learning process 218 may have learned that every time the user attends a wine and cheese party the user deviates from the nutrition regimen and the user's attitude declines. If learning system will then update the rules in the nutrition system 212 to utilize the 204 exogenous data and include rules about wine and cheese parties. The system may also include the ability to utilize exogenous data to then lookup the place, neighborhood, time, the next action of the user's nutrition and appetite plan, such as what the user is to consume that night, and other such information to determine a correct food the user should consume, a store, a restaurant, and/or a correct output 224 type to send to the user via the client device 102 based upon the exogenous data 204, individual user profile 202, crowd data 206, aggregate profile 208, and the user's nutrition and appetite plan. Thus, the learning process 218 can modify the user's experience, including motivational messages to send to the user as output 224, and nutrition and appetite plan to best suit the user based on past user experiences.

The learning process 218 can modify the output 224, based upon what types of messages including the content, style, and form such as audio, textual, or visual, are effective based upon the exogenous data 204, individual user profile 202, crowd data 206, aggregate profile 208, and the user's nutrition and appetite plan. Thus, the learning process 218 learns what techniques including motivations are effective, and the correct balance of positive and negative reinforcement to optimize the effectiveness of all the rules in the system including the nutrition and appetite plan and the user's experience.

The learning process 218 can modify the parameters of the user's nutrition and appetite plan and motivation message calculator 228 to optimize output 224 based upon the individual user profile 202. As an example, if according to the user's nutrition and appetite plan the user is to consume fish, the learning process 218 can determine which type of fish the user should consume and/or which type of fish the user should not consume based upon the individual user profile 202 and the user's input 200. As an example, if the user was prompted to consume tuna in the past and the tuna consuming success was low or below a threshold level, and/or the user's reaction to the tuna was negative/user had a negative attitude toward the tuna, then the learning process 218 can lower the user's receptivity to tuna and raise the user's receptivity with regard to other substitute types of fish. Thus, the next time the user is to consume fish according to the user's nutrition and appetite plan the user should not be prompted to consume tuna. In this example the learning process 218 relies on the fact that the rules in the instance of the nutrition and behavior rules 212 are parameterizable so they can be adjusted, evolved and modified.

The learning process 218 can modify the parameters of the binge preventer 222, including the parameters of the threshold detector 500. In this illustrative embodiment the learning process 218 can modify the binge preventer 222 through three actions, a spot it action, a prevent it action, and a cure it action. The spot it action involves learning the metrics from the exogenous data 204, individual user profile 202, crowd data 206, aggregate profile 208 to predict when a binge may occur. The prevent it action involves learning what output 224 type can prevent binging activity. The cure it action involves learning what and how to restore the equilibrium state of the nutrition and appetite plan to drive the user back on track with the user's nutrition and appetite plan. The learning action may be communicated to the threshold detector 500 of the binge preventer 222 to allow the binge preventer 222 to accurately spot, prevent, and cure binging activity. Thus, the learning process 218 can predict, prevent, and cure binging activity of a user based on the exogenous data 204, individual user profile 202, crowd data 206, aggregate profile 208 to enhance the effectiveness of the user's nutrition and appetite plan.

The learning process 218 seeks to classify sequences of actions recorded and generated by the computer based system 100 against a series of inputs including a choice of nutrition regimen template, initial profile data, external data, past actions in order to measure the individual user and combined efficacy. The field of computational machine learning provides a number of supervised and un-supervised technologies to improve systems based on examination of empirical data or trial sets with known outcomes. The computer based system 100 disclosed herein generates such data by constantly monitoring the efficacy of the computer based system 100 in regards to achieving goals and the best path to achieve such goals.

The learning process 218 allows the computer based system 100 to learn on a micro level analyzing the efficacy of an instance of behavioral and nutrition template, but also on a macro or "crowd" level by refining all the actions against all the inputs of all the users of the computer based system 100 to learn across like circumstances.

Figure 8A:
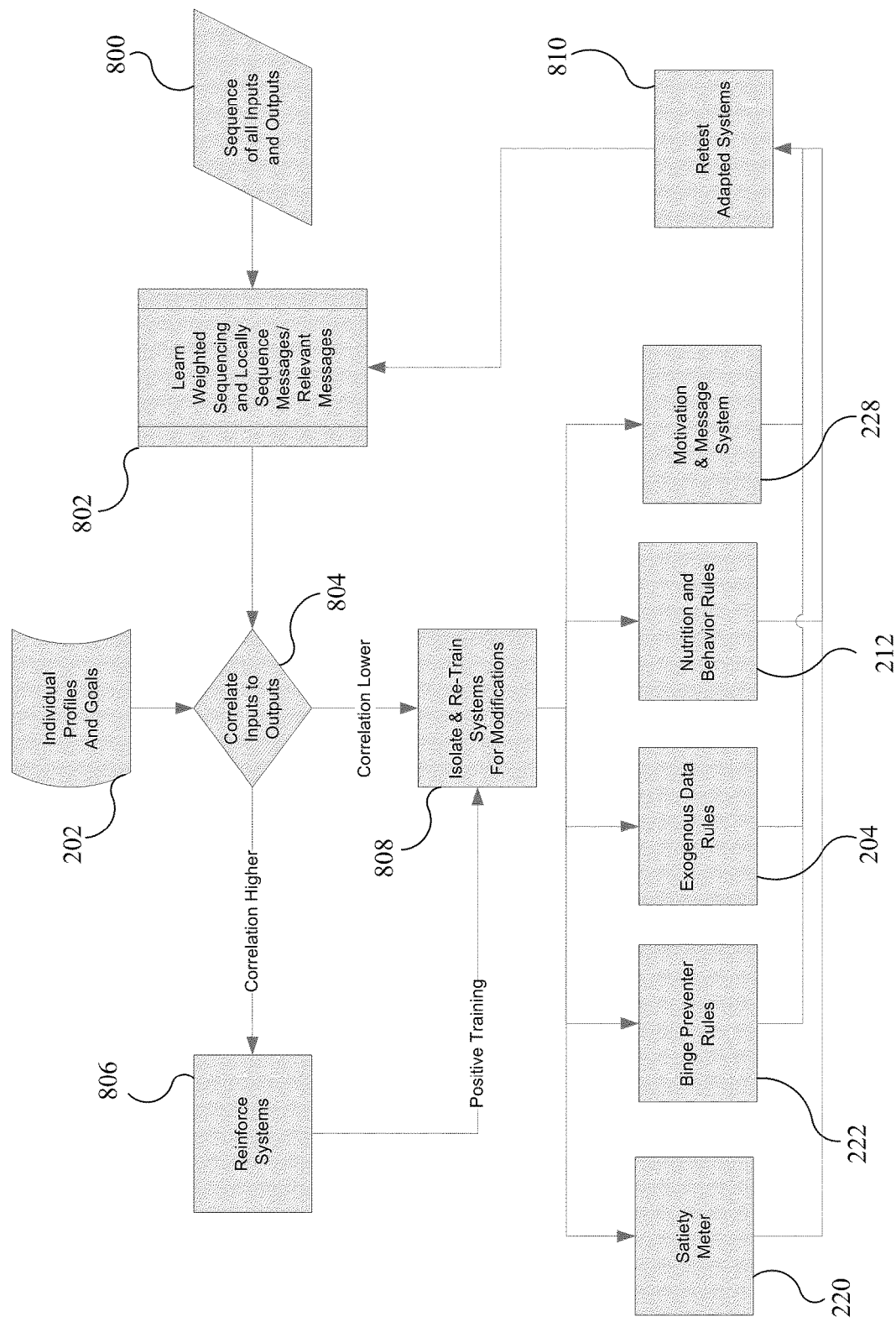
FIGS. 8A-8B illustrate block and flow diagrams of an embodiment of an internal process of the learning process of the computer based system.
Figure 8B:
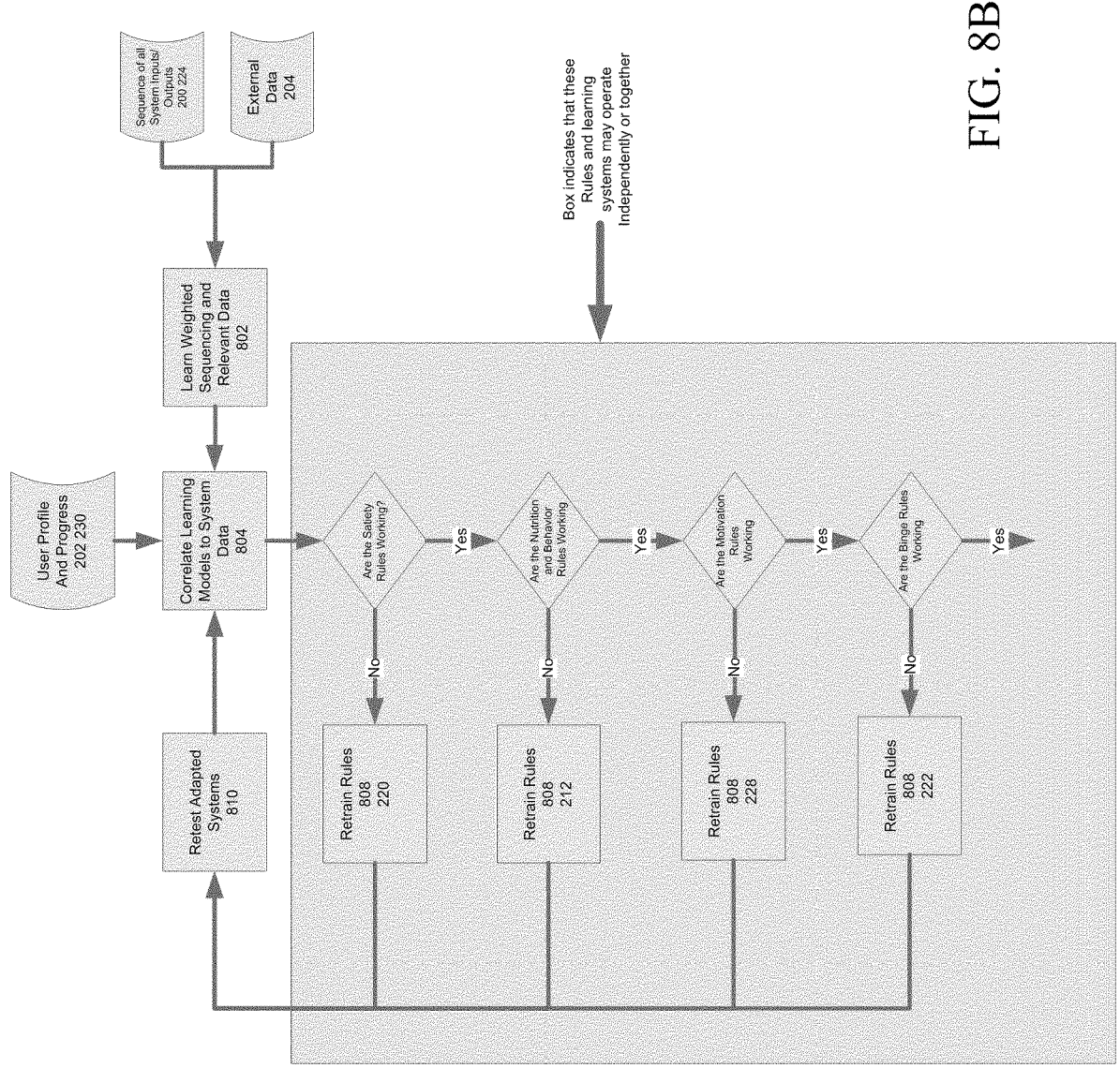

In an illustrative embodiment, an internal process of the learning process 218 is described with reference to FIGS. 8A and 8B. For an individual user the set of all actions, both inputs 200 and outputs 224 are stored in the individual user profile 202. Inputs 200 include, for example, any information gained by the system including things input by the user, information gathered by devices or telemetry systems. Outputs 224 include, for example, messages sent back to the user—and sometimes those messages will attempt to engender additional inputs. For example, the system might ask the user how the user is feeling about a nutrition program or the user's weight. The individual user profile 202 also stores the initial goals of the user, any external data input into the computer based system 100 and relevant crowd data 206. The individual user profile 202 also may record any outputs 224, such as messages sent to the user. After each sequence of inputs 200, the decision engine 214 may calculate an output action 224 and monitor what the local response to that output may be. The learning process 218 obtains a sequence of all the inputs 200 and outputs 224, illustrated as 800.

The learning process 218 then processes the sequence 800 to learn weighted sequencing and locally sequence messages in terms of relevant messages to send to the user, illustrated as 802. More particularly, the learning process 218 determines how many of the inputs 200 and outputs 224 in sequence 800 are relevant at the current moment; also known as the depth of the sequence. The learning process 218, weighs the sequence, at 802, using machine learning techniques. These types of learning systems generally include decision trees, Bayesian Learning Networks, Markov Models, Support Vectors, Gaussian Mixture models, and/or regression systems. One consideration in learning is how long a sequence is relevant to analyze each time the computer based system 100 learns and that too may be learned. It can be appreciated that in some cases learning a year ago may be very relevant in some cases and in other cases not at all, and visa versa.

After the learning process 218 processes the sequence 800, the learning process 218 processes the locally sequenced messages 802 along with the individual user profile 202 and goals to determine the nature of the correlation of the locally sequenced inputs 200 to outputs 224, illustrated as 804. In an illustrative embodiment, the data is analyzed by the learning process 218, at 804, using the machine learning techniques including the Gaussian classifiers, decision trees, neural networks, Bayesian networks, Markov models and/or other similar techniques, to determine how to correctly identify the effectiveness of the outputs 224 in driving behavior and correlation to the inputs 200.

If the latest collection of inputs 200 and outputs 224 correlate well, or have a high correlation, to the individual user profile 202, then the data is used to reinforce 806 the system rules and weights. For example, to reinforce 806 the rules the learning process 218 may retrain the computer based system 100, illustrated as 808, to keep the rules the same and/or increase the weight given to those rules. More particularly, the learning process 218 may isolate each of the rules associated with each of the exogenous data 204, binge preventer 222, nutrition engine 212, message calculator 228, and satiety meter 220 and reinforce those rules.

Alternatively, if the latest collection of inputs 200 and outputs 224 do not correlate well, or have a low correlation, to the individual user profile 202, then the learning process 218 learns and retrains 808 the various rules systems that operate (in some implementations independently) including the rules associated with each of the exogenous data 204, binge preventer 222, nutrition engine 212, satiety meter 220 and message calculator 228. More particularly, the learning process 218 may isolate each of the rules associated with each of the exogenous data 204, binge preventer 222, nutrition engine 212, 220 satiety meter and message calculator 228, and update or modify those rules in accordance with what was learned. Multiple rule sets may have to be updated after the learning occurs and it is expected that this process may be run multiple times to identify the best fit by using multiple passes of multiple algorithms.

Once the system completes the optimal editing of the rules or other logical representations of the logic that controls the modules, the learning process 218 retests 810 the new modules against the individual user profile 202 to ensure that the update, modification, and/or editing of the rules was effective, for example resulting in a high correlation of inputs 200 and outputs 224 to the individual user profile 202. All this processing can take place in the 100 network based device to not create performance issues and to be able to apply these techniques for multiple users.

It should be appreciated that any divergence between the proposed result and the next input result creates more classification data for the learning system to analyze. For example if the exogenous data 204 inputs to the individual user profile 202 that a cocktail party is occurring this evening the decision engine 214 governed by the nutrition engine 212 and the motivation message calculator 228 may decide to send a message to the user to eat something prior to the cocktail party. If the computer based system 100 learns from the user that this prophylactic eating did not occur the computer based system 100 could choose to change the type of message (aural, textual, visual), change the time the message sent, change the number of times the message was sent, and/or change the content of the message. Each time, the computer based system 100 learns and attempts to modify the outputs 224 to increase their efficacy. Thus, as the sequence of inputs 200 and/or outputs 224 grows the computer based system 100 will continually monitor other like profile signatures including rules to see if what is learned from the third party user is applicable to improve the local user's profile or permanently update the initial instances of the rules. Over time this will insure the computer based system's 100 performance will continually improve as more users interact with the system.

Figure 9A:
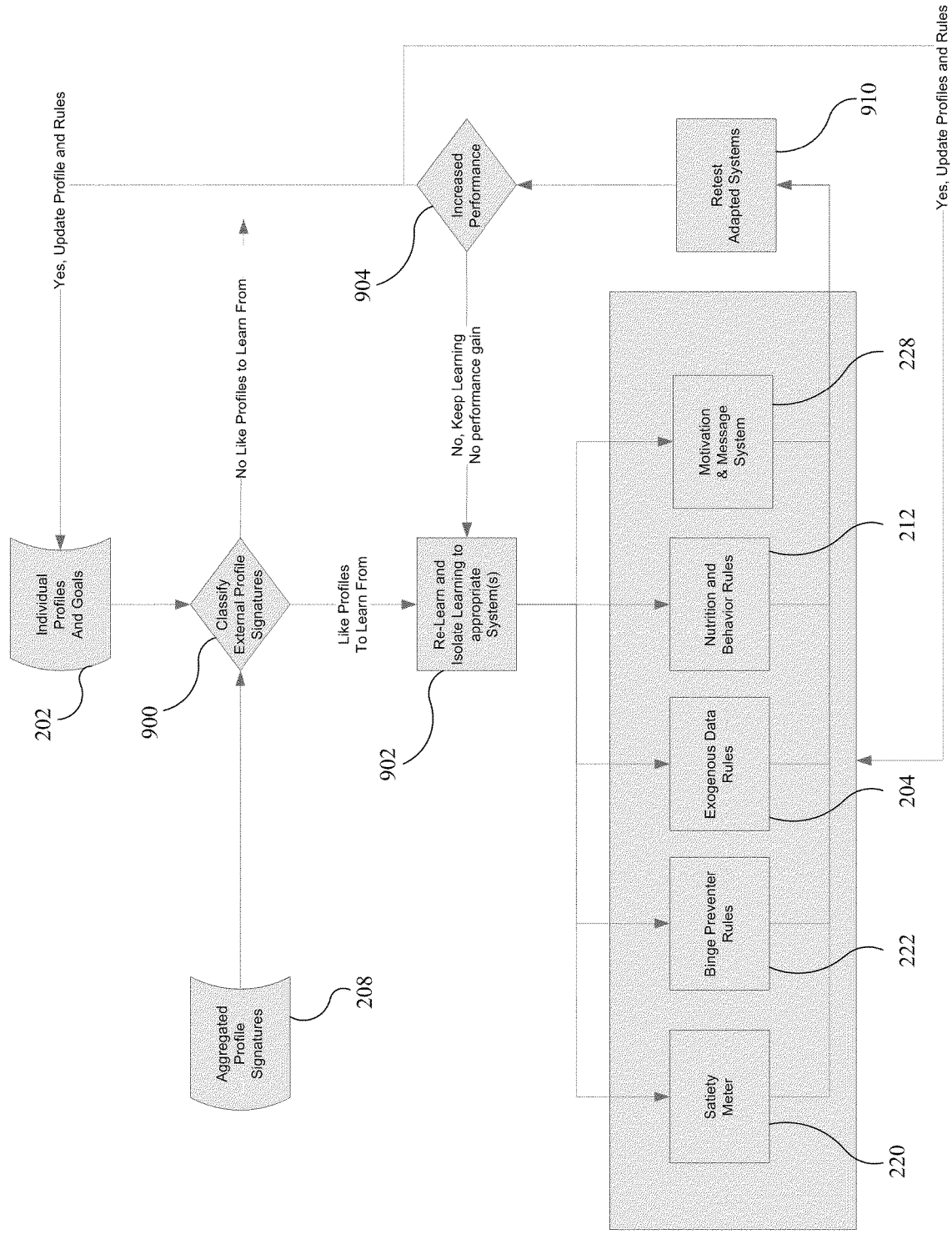
FIGS. 9A-9B illustrate block and flow diagrams of an embodiment of another internal process of the learning process of the computer based system.
Figure 9B:
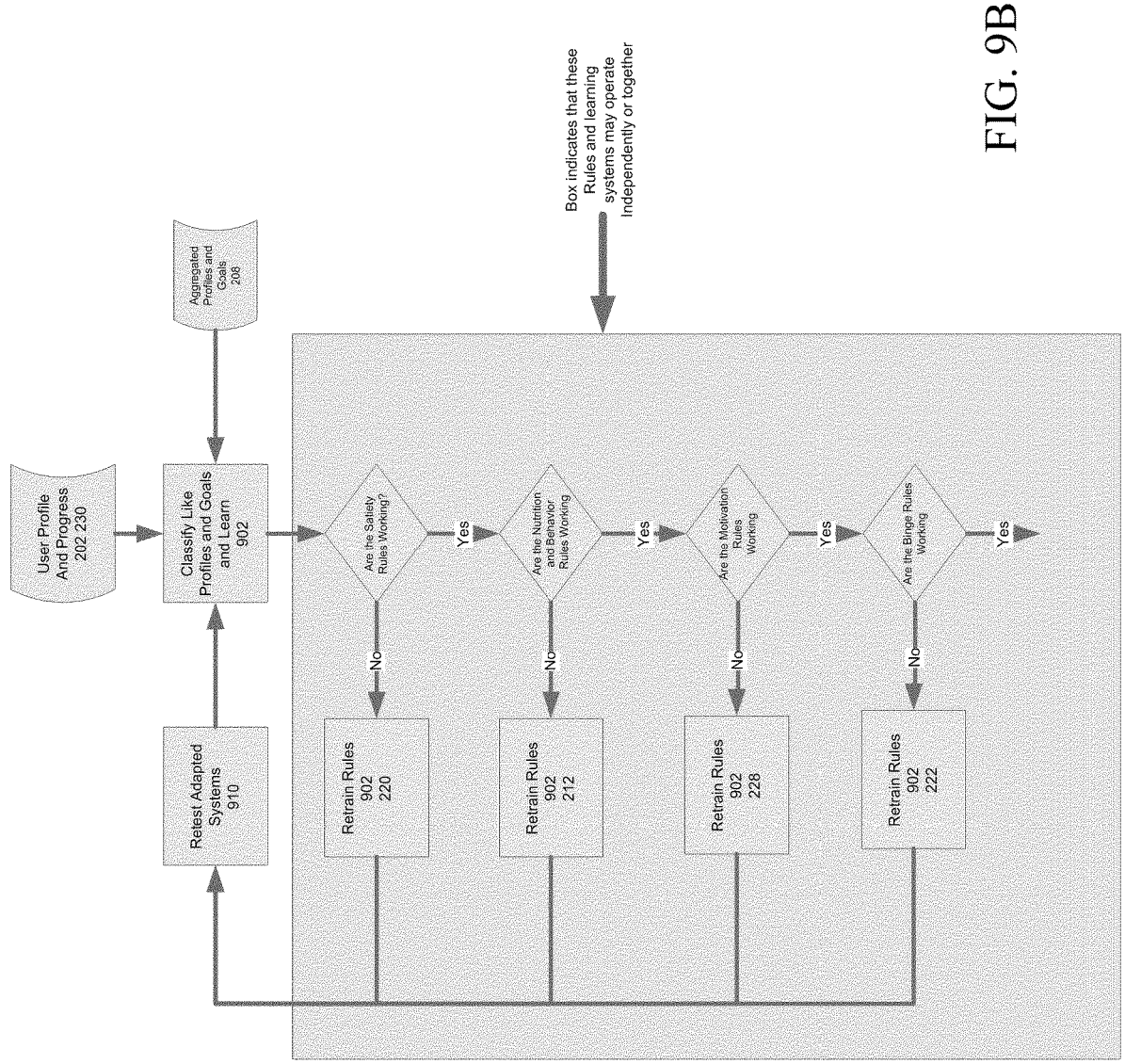

In an illustrative embodiment, another internal process of the learning process 218 is described with reference to FIGS. 9A and 9B. In the same fashion, as discussed above, the computer based system 100 collects multiple profiles of users of the system, crowd data 206, and constantly refines the individual user profile 202 by matching them against like profiles, forming aggregate profile signatures 208, including the various rules modules to determine the optimization learning across multiple user profiles. As used herein, like profiles include profiles of third party users whose profiles share common attributes with the user's individual user profile 202. As illustrated in FIGS. 9A and 9B, the learning process 218 identifies and classifies 900 the set of like profiles that can be used to improve the functioning of the user's individual user profile 202. This comparison process includes examining not just the individual user profile 202 and goals but also the aggregate profile signatures 208 of like profiles and how all the users respond to the outputs 224 of the computer based system 100 as reflected in the learning that has taken place across the system including but not limited to the binge preventer 222, nutrition and behavior rules 212, motivation message system 228, satiety meter 220 and the exogenous data 204 and the rules of how to respond to it.

Once like profiles have been identified the system can then improve and relearn 902 the individual users rules (as used herein, rules include not just formal rules systems but any systems that can convey logical rules including but not limited to graphs, perceptrons, decision trees, classifiers, Markov chains or the like). More particularly, the learning process 218 may isolate each of the rules associated with each of the exogenous data 204, binge preventer 222, nutrition engine 212, satiety meter 220, and message calculator 228, and update or modify those rules in accordance with what was learned. Multiple rule sets may have to be updated after the learning occurs and it is expected that this process may be run multiple times to identify the best fit by using multiple passes of multiple algorithms.

The like profiles act like example data for retraining on the individual user's profile 202 continually to improve the performance 904 until it reaches an optimal result with the current data sets. As an example it may be for a certain type of profile that Valentine's Day causes people to binge. However, if a new user begins the system in the fall by learning from like profiles the computer based system 100 can be forewarned that it should be on the alert for a binge and try to prevent one even if the individual user's profile has nothing to indicate that a date will be problematic. Thus, the learning process 218, in FIGS. 9A and 9B, can allow a new user to learn from the experience of others.

As more users use the system for the entire network of profiles will become smarter as the system generalizes across a number of like profiles. Just as in FIGS. 8A and 8B, the learning is applied across all the appropriate rules modules and the system is retested 910 to make sure the historical data still correlates. More particularly, once the system completes the optimal editing of the rules or other logical representations of the logic that controls the modules, the learning process 218 retests 910 the new modules against the individual user profile 202 to ensure that the update, modification, and/or editing of the rules was effective.

While the learning process 218 has been described above as modifying certain parameters and processes within the computer based system 100 it should be appreciated that the learning process can be applied to any of the parameters, processes, and other parts of the computer based system 100 to optimize the user's nutrition and appetite plan and experience.

It should be appreciated that the computer based system 100 may include additional communication networks. For example, the computer based system 100 may include a buddy system, wherein a user is paired up with one or more users and can communicate with each other, via the client device(s) 102, through the computer based system 100 to encouraging each other to stay with the nutrition and appetite plan and/or regimen either directly or perhaps through a social network. In another example, the computer based system 100 may include a communication platform wherein the user may communicate, via the client device 102, directly with a live human being for encouragement, motivation, and/or other advice.

Figure 10A:
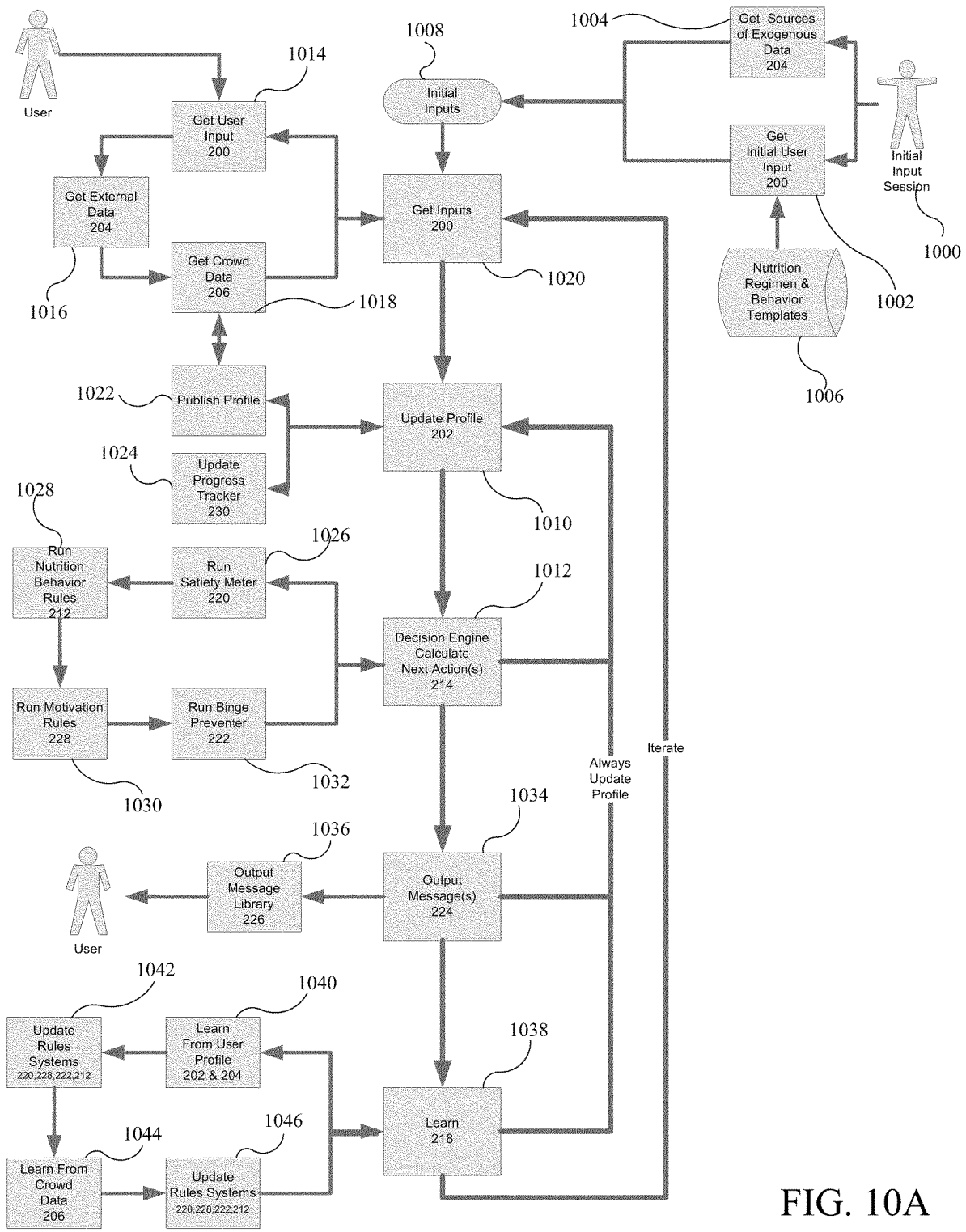
FIGS. 10A-10B illustrate flow and state diagrams of a method for monitoring and analyzing the physiological and mental state of nutrition and optimizing nutritional intake.
Figure 10B:
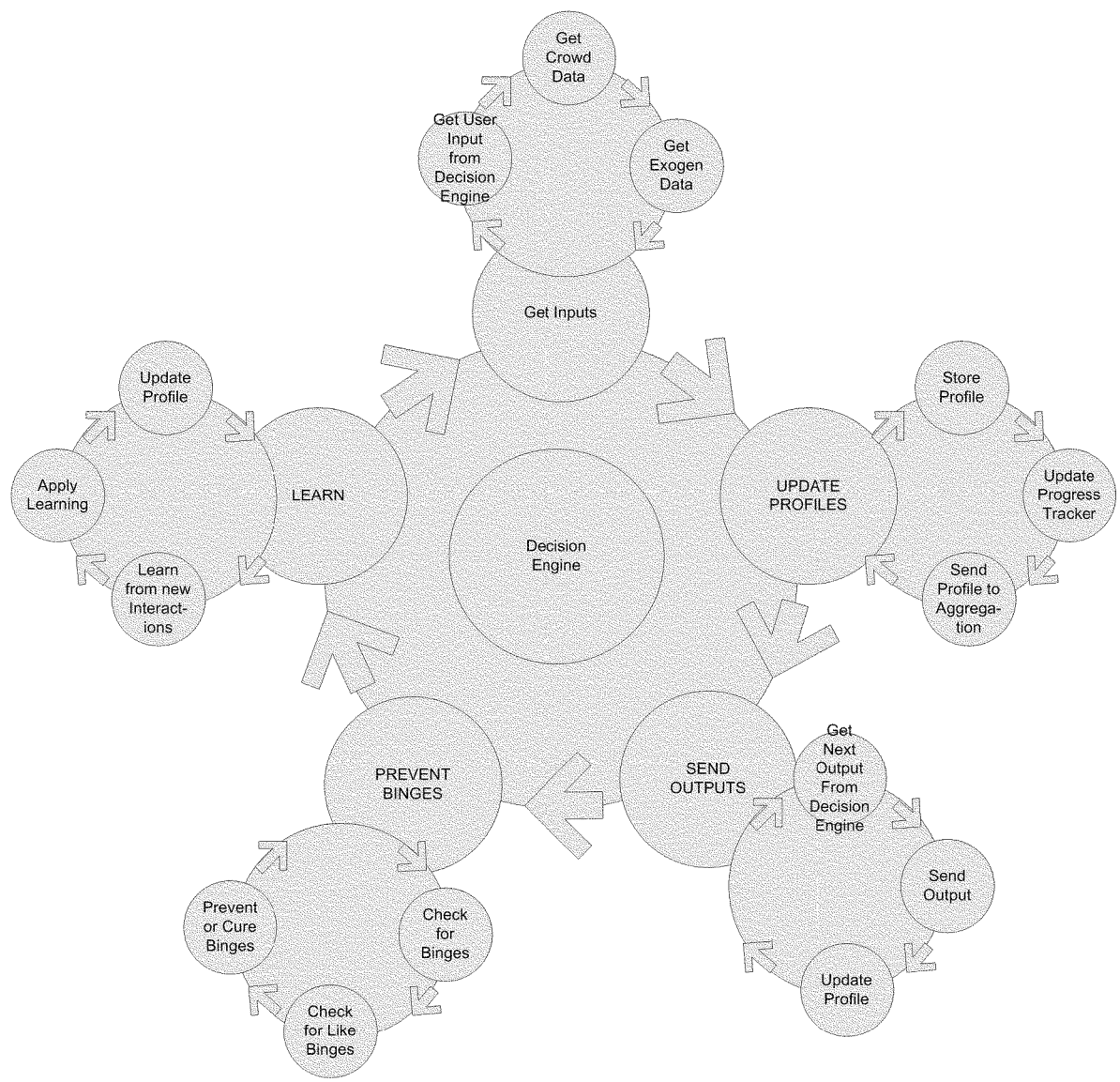

A block flow diagram of a method for monitoring and analyzing the physiological state of nutrition and optimizing nutritional intake according to an illustrative embodiment is described with reference to FIGS. 1, 2, 10A, and 10B. To begin a diet or nutritional plan, the user may access the user interface via the client device 102 and begin an initial input session 1000 to create a profile in the computer based system 100, such as the profile 202 described above. To create the profile the user may input data via the client device 102, such as input data 200 described above, provide the computer based system 100 access to exogenous data, such as the exogenous data 204 described above, and/or choose a nutrition and appetite plan, such as through the use of the nutrition engine 212 described above. As illustrated in FIGS. 10A and 10B, the computer based system 100 obtains 1002 the initial user input data 200, and obtains 1004 sources of exogenous data 204. Further, the computer based system 100 obtains 1006 the user's choice of nutrition and appetite regimen as part of obtaining 1002 the initial user input data 200. The computer based system 100 then takes all of the initial inputs 1008 and creates a user profile for the user 1010.

The profile may be received 1012 by the decision engine 214, which monitors, analyzes, and updates the user's profile. The decision engine 214 may obtain real-time input (for example, via prompting the user), such as what the user has consumed, when the food was consumed, how the user feels, the user's attitude, and other such information as described above as input data 200. As illustrated, the computer based system 100 may obtain 1014 real-time and/or non-real-time input from the user, obtain 1016 external or exogenous data 204, and obtain 1018 crowd data 206 throughout the nutrition regimen. All of the data obtained by the computer based system 100 can continuously be combined 1020 and used to update/create 1010 the user profile.

In an illustrative embodiment, the user profile may be published 1022 by the computer based system 100 to be used as part of the crowd and the profile may be enhanced by accessing 1018 crowd data 206 from other users. The user profile may also be used 1024 by the progress tracker 230 to continuously monitor and update the progress of the user throughout the user's nutrition regimen.

The decision engine 214 may then communicate and/or transmit the user profile to the satiety meter 220, nutrition engine or nutrition and behavior rules 212, motivation message calculator 228, and binge preventer 222. One or more of the satiety meter 220, nutrition engine or nutrition and behavior rules 212, motivation message calculator 228, and binge preventer 222 may then be run, illustrated as 1026, 1028, 1030, and 1032, respectively. More particularly, one or more of the satiety meter 220, nutrition engine or nutrition and behavior rules 212, motivation message calculator 228, and binge preventer 222 may consult with its model and/or the scientific data and/or rules to determine a suggested next action for the user. One or more of the satiety meter 220, nutrition engine or nutrition and behavior rules 212, motivation message calculator 228, and binge preventer 222 may then communicate and/or transmit the suggested next action to the decision engine 214. The decision engine 214 may then consult with the user's nutrition and appetite plan and determine what actions the system should make including whether to instruct the user to consume food and/or when to consume food to prevent the user from experiencing a feeling of hunger or to send a user queries to get more information.

In an illustrative example, the decision engine 214 may communicate or transmit the user's input data and profile to the satiety meter 220. The satiety meter 220 may receive the user input data 200 and individual user profile 202 information, such as the user's physiological information. The satiety meter 220 may be run 1026 and assay the user input data 200 and individual user profile 202 and establish a baseline nutritional or appetite state of the user. For example, the baseline nutritional or appetite state may be determined by assessing fasting versus feasting nutritional states, averaging nutritional states of the user over a period of time, and using a generic model of human metabolism. Establishment of the baseline nutritional state may allow the computer based system 100 to adapt to the unique nutritional physiology of a given user, which is an important aspect because nutritional physiology varies significantly with a number of factors including, but not limited to, body mass, gender, and age.

The decision engine 214 may also obtain real-time and/or non-real-time input, illustrated as 1014, via prompting a user to enter input via the client device 102, such as what the user has consumed, when the food was consumed, how the user feels, the user's attitude, planned and/or performed activities, and other such information as described above as input data 200. The decision engine 214 may communicate and/or transmit the user's real-time and/or non-real-time input to the satiety meter 220. The satiety meter 220 may assay and monitor the user's profile 202 including the nutritional state of the user based on the real-time input data. This monitoring may be completed at designated time intervals, or in real time. The satiety meter 220 may compare the user's profile 202 including the nutritional state of the user to the baseline nutritional state of the user and analyze the states, according to the scientific data and/or rules 216, to determine a differential value. The differential value may be correlated with established goals to anticipate the nutritional needs of the user. The satiety meter 220 may then preemptively determine the appropriate nutritional intake of the user to prevent the onset of hunger.

The satiety meter 220 may communicate and/or transmit the determined appropriate nutritional intake of the user to the decision engine 214. The decision engine 214 may then consult with the user's nutrition and appetite plan and determine whether to instruct the user to consume food and/or when to consume food to prevent the user from experiencing a feeling of hunger. Then the decision engine may communicate 1034 with the messages 226 held in a database and the motivation message calculator 228 to construct a message to be sent 1036 to the user as output, via the client device 102, informing the user of when and what to consume to prevent the onset of hunger, and/or to keep the user on track with the user's nutrition and appetite plan and/or regimen. Prior to sending the message to the user, via the client device 102, the message may be passed through a psychology filter to ensure the message medium and content is maximally motivational, which may be a function of the message calculator 228. Then the decision engine may send 1036 the message to the user, via the client device 102, as output 224. The output 224 may be communicated to the user, via the client device 102, through the user interface.

The satiety meter 220 may then enter a feedback loop that may monitor the basic rhythm of hunger in a user at the physiological level over the course of time, and anticipate the onset of hunger of the user by monitoring changes in nutritional related physiological cues.

The motivation message calculator 228 and binge preventer 222 may also be run, illustrated as 1030 and 1032, respectively. As each of the motivation message calculator 228 and binge preventer 222 are run each may consult with its respective model and/or the scientific data and/or rules to determine a suggested next action for the user. Each of the motivation message calculator 228 and binge preventer 222 may then communicate and/or transmit its respective suggested next action to the decision engine 214. The decision engine 214 may then consult with the user's nutrition and appetite plan and determine what actions the system should make, as described above. Although, the satiety meter 220, nutrition engine or nutrition and behavior rules 212, motivation message calculator 228, and binge preventer 222 are illustrated as running in series, it should be appreciated that each of satiety meter 220, nutrition engine or nutrition and behavior rules 212, motivation message calculator 228, binge preventer 222, and any other process described herein, may be run independently, in series, in parallel, or any combination thereof.

Further, the decision engine 214 and progress tracker 230 may track the progress of the user as the user inputs data and responds to the output 224, illustrated as 1014. The progress data, user input data, user profile, exogenous data, and reactions of the user to the output data may be combined with the crowd data, such as the crowd data 206 described above. As discussed above, the computer based system 100 may obtain 1014 real-time input from the user, obtain 1016 external or exogenous data 204, and obtain 1018 crowd data 206 throughout the nutrition regimen. All of the data obtained by the computer based system 100 can continuously be combined 1020 and used to update/create 1010 the user profile.

The combined data may be communicated and/or transmitted 1038 to the learning process 218. The learning process 218 may analyze the combined data along with the user's progress data, input data, and profile to determine how the user is reacting and/or adapting to the user's nutrition and appetite plan. The learning process 218 may learn 1040 and modify and/or update the parameters of the user's nutrition and appetite plan based on the user's profile 202 and exogenous data 204. The learning process 218 may learn 1042 and modify and/or update the rules associated with any of the satiety meter 220, motivation message calculator 228, binge preventer 222, and nutrition engine or nutrition and behavior rules 212 to ensure the user's nutrition and appetite plan and experience is maximized. The learning process 218 may learn 1044 and modify and/or update the parameters of the user's nutrition and appetite plan based on the crowd data 206. More particularly, the learning process 218 may learn 1046 from the crowd data and modify and/or update the rules associated with any of the satiety meter 220, motivation message calculator 228, binge preventer 222, and nutrition engine or nutrition and behavior rules 212 to ensure the user's nutrition and appetite plan and experience is maximized. The learning process 218 continuously iterates over the system and continuously updates the user's profile and experience to maximize the effectiveness of the user's nutrition and appetite regimen and experience.

While the illustrative embodiments are described with regard to implementation of diet/weight-loss goals, one skilled in the art will appreciate that this disclosure can also be used to achieve specific nutrition related goals. For example, the present disclosure may be implemented to optimize the nutritional intake of an Individual for specific reasons, like body building or endurance training Additionally, for example, the present disclosure could also be used as a survival aid by soldiers to maximize the nutritional value of a limited food supply in a survival situation.

While the present disclosure has been described and illustrated in connection with preferred embodiments, many variations and modifications will be evident to those skilled in the art and may be made without departing from the spirit and scope of the present disclosure. The present disclosure is thus not to be limited to the precise details of methodology or construction set forth above as such variations and modification are intended to be included within the scope of the present disclosure.

The invention claimed is:

1. A system for proactively notifying a user of a nutritional need, the system comprising:
    a database storing a plurality of nutrition regimen templates, each nutrition regimen template comprising a set of parameters related to a nutrition regimen and collecting and storing collective crowd information and data from other users similar to the user;
    an input/output processor configured to receive input data from and transmit messages to the user, the input/output processor including a user interface adapted to allow the user to input the input data;
    a nutrition processor configured to receive the input data from the user, exogenous data, and a nutrition regiment template and generate a parameterized nutrition regimen, and modify the parameterized nutrition regimen template for the current user based, at least in part, upon the collective crowd information and data and rules that were effective with other users similar to the user;
    a satiety processor configured to generate a dynamic user profile for the user including a baseline nutritional state based on the input data and monitor a present nutritional state of the user, the present nutritional state generated from at least one of the input data, historical data relating to prior nutritional states of the user, and exogenous data;
    a learning processor configured to:
        assay the input data, historical data relating to prior nutritional states of the user, and exogenous data,
        estimate a future nutritional state, and
        adapt the parametrized nutrition regimen based on, at least:
            the assayed input data, historical data and exogenous data,
            determining whether the user comprehended the transmitted messages,
            determining whether the user followed instructions in the transmitted messages, and
            determining whether following the instruction in the transmitted messages was effective;
    a decision processor configured to receive input from the learning processor, the nutrition processor and the satiety processor, the decision processor further configured to generate a proactive alert based on the future nutritional state of the user compared to the baseline nutritional state, the proactive alert sent to the input/output processor for transmission to the user.

2. The system of claim 1, wherein said decision processor is configured to cause said proactive alert to be based at least upon a user profile, nutritional and other rules and other nutritional plans stored in said database.

3. The system of claim 1, wherein said decision processor is further configured to calculate a next action in anticipation of an event based upon solely non-physiological input data.

4. The system of claim 1, wherein said satiety processor is further configured to monitor a basic rhythm signal of at least one of hunger, attitude, and activity of said user based on said input data.

5. The system of claim 3, wherein said input/output processor is further configured to transmit said next action to said nutrition processor regarding said user for informing said user what and when to consume prior to an onset of hunger based at least in part on non-physiological input information stored in said database.

6. The system of claim 4, wherein said nutritional processor is further configured to modify said individualized nutritional regimen template, based on said user's inputs, when the inputs are determined to indicate at least one of that the user is failing to follow the plan or failing to meet anticipated plan goals.

7. The system of claim 5, wherein said nutrition processor is further configured to anticipate and modify said individualized nutritional regimen template in accordance with a plurality of short term goals determined by the server to lead to a long term goal.

* * * * *